US009492797B2

(12) United States Patent
Makarewicz et al.

(10) Patent No.: US 9,492,797 B2
(45) Date of Patent: *Nov. 15, 2016

(54) SYSTEM FOR DETECTION OF SPACED DROPLETS

(71) Applicant: Bio-Rad Laboratories, Inc., Hercules, CA (US)

(72) Inventors: Anthony J. Makarewicz, Livermore, CA (US); Amy L. Hiddessen, Dublin, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 47 days.

This patent is subject to a terminal disclaimer.

(21) Appl. No.: 14/159,410

(22) Filed: Jan. 20, 2014

(65) Prior Publication Data

US 2014/0200164 A1    Jul. 17, 2014

Related U.S. Application Data

(63) Continuation-in-part of application No. 12/586,626, filed on Sep. 23, 2009, now Pat. No. 9,156,010, and
(Continued)

(51) Int. Cl.
*B01F 3/08*        (2006.01)
*B01F 13/00*       (2006.01)
(Continued)

(52) U.S. Cl.
CPC ......... *B01F 3/0807* (2013.01); *B01F 13/0062* (2013.01); *B01L 3/0241* (2013.01);
(Continued)

(58) Field of Classification Search
CPC .......... C12M 23/48; C12M 41/14; B01L 7/00; B01L 7/52; B01L 2300/0829; A61K
(Continued)

(56) References Cited

U.S. PATENT DOCUMENTS

| 3,575,220 A | 4/1971 | Davis et al. |
| 4,051,025 A | 9/1977 | Ito |

(Continued)

FOREIGN PATENT DOCUMENTS

| EP | 1522582 A2 | 4/2005 |
| EP | 1522582 B1 | 7/2007 |

(Continued)

OTHER PUBLICATIONS

Young, Lee W., Authorized officer, International Searching Authority, International Search Report, PCT Application Serial No. PCT/US2009/05317; mailing date: Nov. 20, 2009.

(Continued)

*Primary Examiner* — Michael Hobbs
(74) *Attorney, Agent, or Firm* — Kolisch Hartwell, P.C.

(57) ABSTRACT

Method of detection for droplet-based assays. In an exemplary method, an open end of a channel network may be placed into an emulsion. Droplets of the emulsion may be driven along a flow path from the open end, through a confluence region where a dilution fluid is introduced into the flow path from at least one dilution inlet channel to increase an average distance between droplets, and through an examination region disposed downstream of the confluence region. Light may be detected from the examination region as droplets pass through. The channel network may include a droplet inlet channel that meets the at least one dilution inlet channel at the confluence region. The droplet inlet channel may form a tapered region that is sized such that droplets leave the tapered region in single file.

20 Claims, 12 Drawing Sheets

Related U.S. Application Data a continuation-in-part of application No. 12/862,542, filed on Aug. 24, 2010, now Pat. No. 9,194,861, and a continuation-in-part of application No. 12/890,550, filed on Sep. 24, 2010, now Pat. No. 8,633,015, and a continuation-in-part of application No. 13/245,575, filed on Sep. 26, 2011, now abandoned, and a continuation-in-part of application No. 13/945,661, filed on Jul. 18, 2013, and a continuation-in-part of application No. 12/962,507, filed on Dec. 7, 2010, now Pat. No. 9,216,392, and a continuation-in-part of application No. 12/962,511, filed on Dec. 7, 2010, and a continuation-in-part of application No. 12/962,502, filed on Dec. 7, 2010, now Pat. No. 9,248,417, and a continuation-in-part of application No. 12/963,523, filed on Dec. 8, 2010, now Pat. No. 9,126,160, and a continuation-in-part of application No. 13/039,233, filed on Mar. 2, 2011, now Pat. No. 8,709,762, and a continuation-in-part of application No. 12/976,827, filed on Dec. 22, 2010, and a continuation-in-part of application No. 13/341,669, filed on Dec. 30, 2011, and a continuation-in-part of application No. 13/341,678, filed on Dec. 30, 2011, now Pat. No. 8,730,479, and a continuation-in-part of application No. 13/072,673, filed on Mar. 25, 2011, now Pat. No. 9,132,394, and a continuation-in-part of application No. 13/341,688, filed on Dec. 30, 2011, and a continuation-in-part of application No. 13/287,120, filed on Nov. 1, 2011, now Pat. No. 9,089,844, and a continuation-in-part of application No. 13/424,304, filed on Mar. 19, 2012, now Pat. No. 9,222,128, and a continuation-in-part of application No. 13/548,062, filed on Jul. 12, 2012, now Pat. No. 8,951,939, and a continuation-in-part of application No. PCT/US2012/048198, filed on Jul. 25, 2012, and a continuation-in-part of application No. 13/562,198, filed on Jul. 30, 2012, now Pat. No. 8,663,920, and a continuation-in-part of application No. 13/287,095, filed on Nov. 1, 2011, now abandoned, and a continuation-in-part of application No. 13/863,231, filed on Apr. 15, 2013, said application No. 12/890,550 is a continuation-in-part of application No. 12/586,626, said application No. 13/245,575 is a continuation of application No. 12/586,626, said application No. 13/945,661 is a continuation-in-part of application No. 13/251,016, filed on Sep. 30, 2011, and a continuation-in-part of application No. 13/245,575, and a continuation-in-part of application No. 12/976,827, said application No. 12/962,507 is a continuation of application No. 12/586,626, said application No. 12/962,511 is a continuation of application No. 12/586,626, said application No. 12/962,502 is a continuation of application No. 12/586,626, said application No. 12/963,523 is a continuation of application No. 12/586,626, said application No. 13/341,669 is a continuation of application No. PCT/US2011/030101, filed on Mar. 25, 2011, said application No. 13/341,678 is a continuation of application No. PCT/US2011/030077, filed on Mar. 25, 2011, said application No. 13/072,673 is a continuation-in-part of application No. 12/586,626, said application No. 13/341,688 is a continuation of application No. PCT/US2011/030097, filed on Mar. 25, 2011, said application No. 13/287,095 is a continuation-in-part of application No. 12/976,827.

(60) Provisional application No. 61/194,043, filed on Sep. 23, 2008, provisional application No. 61/206,975, filed on Feb. 5, 2009, provisional application No. 61/271,538, filed on Jul. 21, 2009, provisional application No. 61/275,731, filed on Sep. 1, 2009, provisional application No. 61/277,200, filed on Sep. 21, 2009, provisional application No. 61/277,203, filed on Sep. 21, 2009, provisional application No. 61/277,204, filed on Sep. 21, 2009, provisional application No. 61/277,216, filed on Sep. 21, 2009, provisional application No. 61/277,249, filed on Sep. 21, 2009, provisional application No. 61/277,270, filed on Sep. 22, 2009, provisional application No. 61/275,860, filed on Sep. 2, 2009, provisional application No. 61/309,837, filed on Mar. 2, 2010, provisional application No. 61/309,845, filed on Mar. 2, 2010, provisional application No. 61/317,684, filed on Mar. 25, 2010, provisional application No. 61/317,635, filed on Mar. 25, 2010, provisional application No. 61/380,981, filed on Sep. 8, 2010, provisional application No. 61/409,106, filed on Nov. 1, 2010, provisional application No. 61/410,769, filed on Nov. 5, 2010, provisional application No. 61/417,241, filed on Nov. 25, 2010, provisional application No. 61/341,218, filed on Mar. 25, 2010, provisional application No. 61/317,684, filed on Mar. 25, 2010, provisional application No. 61/341,065, filed on Mar. 25, 2010, provisional application No. 61/467,347, filed on Mar. 24, 2011, provisional application No. 61/409,473, filed on Nov. 2, 2010, provisional application No. 61/454,373, filed on Mar. 18, 2011, provisional application No. 61/507,082, filed on Jul. 12, 2011, provisional application No. 61/510,013, filed on Jul. 20, 2011, provisional application No. 61/511,445, filed on Jul. 25, 2011, provisional application No. 61/513,474, filed on Jul. 29, 2011, provisional application No. 61/601,514, filed on Feb. 21, 2012, provisional application No. 61/624,199, filed on Apr. 13, 2012.

(51) Int. Cl.
| | | |
|---|---|---|
| *B01L 3/02* | (2006.01) | |
| *B01L 3/00* | (2006.01) | |
| *B01L 7/00* | (2006.01) | |
| *G01N 15/14* | (2006.01) | |
| *G01N 15/10* | (2006.01) | |

(52) U.S. Cl.
CPC .......... *B01L 3/502784* (2013.01); *B01L 7/525* (2013.01); *G01N 15/1404* (2013.01); *G01N 15/1434* (2013.01); *G01N 15/1459* (2013.01); *G01N 15/1463* (2013.01); *G01N 15/1484* (2013.01); *B01L 2200/0689* (2013.01); *B01L 2300/088* (2013.01); *B01L 2300/0816* (2013.01); *B01L 2300/0819* (2013.01); *B01L 2300/0864* (2013.01); *B01L 2300/1822* (2013.01); *B01L 2400/0478* (2013.01); *B01L 2400/0487* (2013.01); *B01L 2400/0622* (2013.01); *G01N 15/1436* (2013.01); *G01N 2015/1006* (2013.01); *G01N 2015/1415* (2013.01)

(58) Field of Classification Search
CPC ................ 9/113;A61K 9/5089; B01F 3/0807; B01F 5/045; B01F 13/0062; B01F 13/1016; B01F 13/1013; B01F 17/00; B01F 2005/0022; B01J 13/14; Y10T 428/2998

USPC .................................................. 435/303.1
See application file for complete search history.

(56) References Cited

U.S. PATENT DOCUMENTS

| | | |
|---|---|---|
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,427 B1 | 8/2003 | Tu |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,054,244 B2 | 5/2006 | Senno et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 9,132,394 B2 * | 9/2015 | Makarewicz, Jr. ... B01F 3/0807 |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |

(56) References Cited

U.S. PATENT DOCUMENTS

| | | |
|---|---|---|
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0014360 A1 | 1/2009 | Toner et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Costa et al. |
| 2010/0015606 A1 | 1/2010 | Davies et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| GB | 1503163 A | 3/1978 |
| GB | 2097692 A | 11/1982 |
| JP | H0295433 A | 4/1990 |
| WO | 8202562 A1 | 8/1982 |
| WO | 8402000 A1 | 5/1984 |
| WO | 9201812 A1 | 2/1992 |
| WO | 9405414 A1 | 3/1994 |
| WO | 9612194 A1 | 4/1996 |
| WO | 9800231 A1 | 1/1998 |
| WO | 9816313 A1 | 4/1998 |
| WO | 9844151 A1 | 10/1998 |
| WO | 9844152 A1 | 10/1998 |

(56) References Cited

FOREIGN PATENT DOCUMENTS

| | | |
|---|---|---|
| WO | 9847003 A1 | 10/1998 |
| WO | 0107159 A2 | 2/2001 |
| WO | 0112327 A1 | 2/2001 |
| WO | 0223163 A1 | 3/2002 |
| WO | 02060584 A2 | 8/2002 |
| WO | 02068104 A1 | 9/2002 |
| WO | 02081490 A2 | 10/2002 |
| WO | 02081729 A2 | 10/2002 |
| WO | 03016558 A1 | 2/2003 |
| WO | 2005023091 A2 | 3/2003 |
| WO | 03042410 A1 | 5/2003 |
| WO | 03072258 A1 | 9/2003 |
| WO | 2004040001 A2 | 5/2004 |
| WO | 2005007812 A2 | 1/2005 |
| WO | 2005010145 A2 | 2/2005 |
| WO | 2005021151 A1 | 3/2005 |
| WO | 2005055807 A2 | 6/2005 |
| WO | 2005073410 A2 | 8/2005 |
| WO | 2005075683 A1 | 8/2005 |
| WO | 2006023719 A2 | 3/2006 |
| WO | 2006027757 A2 | 3/2006 |
| WO | 2006038035 A2 | 4/2006 |
| WO | 2006086777 A2 | 8/2006 |
| WO | 2006095981 A1 | 9/2006 |
| WO | 2007091228 A1 | 8/2007 |
| WO | 2007091230 A1 | 8/2007 |
| WO | 2007092473 A2 | 8/2007 |
| WO | 2007133710 A2 | 11/2007 |
| WO | 2008021123 A1 | 2/2008 |
| WO | 2008024114 A1 | 2/2008 |
| WO | 2008063227 A2 | 5/2008 |
| WO | 2008070074 A2 | 6/2008 |
| WO | 2008070862 A2 | 6/2008 |
| WO | 2008109176 A2 | 9/2008 |
| WO | 2008109878 A2 | 9/2008 |
| WO | 2008112177 A2 | 9/2008 |
| WO | 2009002920 A1 | 12/2008 |
| WO | 2009015863 A2 | 2/2009 |
| WO | 2009049889 A1 | 4/2009 |
| WO | 2009085246 A1 | 7/2009 |
| WO | 2010001419 A2 | 1/2010 |
| WO | 2010018465 A2 | 2/2010 |
| WO | 2011034621 A2 | 3/2011 |
| WO | 2011079176 A2 | 6/2011 |

OTHER PUBLICATIONS

Young, Lee W., Authorized officer, International Searching Authority, Written Opinion of the International Searching Authority, PCT Application Serial No. PCT/US2009/05317; mailing date: Nov. 20, 2009.

J. Smid-Korbar et al., "Efficiency and usability of silicone surfactants in emulsions," International Journal of Cosmetic Science 12, pp. 135-139, (1990), presented at the 15th IFSCC International Congress, Sep. 26-29, 1988, London.

A. Chittofrati et al., "Perfluoropolyether microemulsions," Progress in Colloid & Polymer Science 79, pp. 218-225, (1989).

Steven A. Snow, "Synthesis and Characterization of Zwitterionic Silicone Sulfobetaine Surfactants," Langmuir, vol. 6, No. 2, American Chemical Society, pp. 385-391, (1990).

Polydimethylsiloxane, 5 pgs., published in FNP 52 (1992).

Russell Higuchi et al., "Kinetic PCR Analysis: Real-time Monitoring of DNA Amplification Reactions," Bio/Technology vol. II, pp. 1026-1030, Sep. 11, 1993.

D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).

Y. Sela et al., "Newly designed polysiloxane-graft-poly (oxyethylene) copolymeric surfactants: preparation, surface activity and emulsification properties," Colloid & Polymer Science 272, pp. 684-691, (1994).

M. Gasperlin et al., "The structure elucidation of semisolid w/o emulsion systems containing silicone surfactant," International Journal of Pharmaceutics 107, pp. 51-56, (1994).

Mieczyslaw A. Piatyszek et al., "Detection of telomerase activity in human cells and tumors by a telomeric repeat amplification protocol (TRAP)," Methods in Cell Science 17, pp. 1-15, (1995).

Anthony P. Shuber et al., "A Simplified Procedure for Developing Multiplex PCRs," Genome Research, published by Cold Spring Harbor Laboratory Press, pp. 488-493, (1995).

A. V. Yazdi et al., "Highly Carbon Dioxide Soluble Surfactants, Dispersants and Chelating Agents," Fluid Phase Equilibria, vol. 117, pp. 297-303, (1996).

Ariel A. Avilion et al., "Human Telomerase RNA and Telomerase Activity in Immortal Cell Lines and Tumor Tissues," Cancer Research 56, pp. 645-650, Feb. 1, 1996.

Shuming Nie et al., "Optical Detection of Single Molecules," Annu. Rev. Biophys. BiomoL. Struct., vol. 26, pp. 567-596, (1997).

Edith J. Singley et al., "Phase behavior and emulsion formation of novel fluoroether amphiphiles in carbon dioxide," Fluid Phase Equilibria 128, pp. 199-219, (1997).

Olga Kalinina et al., "Nanoliter scale PCR with TaqMan Detection," Nucleic Acids Research, vol. 25, No. 10 pp. 1999-2004, (1997).

Zhen Guo et al, "Enhanced discrimination of single nucleotide polymorphisms by artificial mismatch hybridization," Nature Biotechnology vol. 15, pp. 331-335, Apr. 1997.

E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.

Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.

Bert Vogelstein et al., "Digital PCR," Proc. Natl. Acad. Sci. USA, vol. 96, pp. 9236-9241, Aug. 1999.

Anthony J. O'Lenick, Jr., "Silicone Emulsions and Surfactants," Journal of Surfactants and Detergents, vol. 3, No. 3, Jul. 2000.

N. Garti et al., "Water Solubilization in Nonionic Microemulsions Stabilized by Grafted Siliconic Emulsifiers," Journal of Colloid and Interface Science vol. 233, pp. 286-294, (2001).

Shinji Katsura et al., "Indirect micromanipulation of single molecules in water-in-oil emulsion," Electrophoresis, vol. 22, pp. 289-293, (2001).

Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).

Hidenori Nagai et al., "Development of a Microchamber Array for Picoliter PCR," Analytical Chemistry, vol. 73, No. 5, pp. 1043-1047, Mar. 1, 2001.

Christopher B. Price, "Regular Review Point of Care Testing," BMJ, vol. 322, May 26, 2001.

3M Specialty Materials, "3M Fluorinert Electronic Liquid FC-3283," product information guide, issued Aug. 2001.

Ivonne Schneegaβ et al., "Miniaturized flow-through PCR with different template types in a silicon chip thermocycler," Lab on a Chip, vol. 1, pp. 42-49, (2001).

Randla M. Hill, "Silicone surfactants—new developments," Current Opinion in Colloid & Interface Science 7, pp. 255-261, (2002).

Richard M. Cawthon, "Telomere measurement by quantitative PCR," Nucleic Acids Research, vol. 30, No. 10, pp. 1-6, (2002).

Anfeng Wang et al., "Direct Force Measurement of Silicone- and Hydrocarbon-Based ABA Triblock Surfactants in Alcoholic Media by Atomic Force Microscopy," Journal of Colloid and Interface Science 256, pp. 331-340 (2002).

Shelley L. Anna et al., "Formation of dispersions using "flow focusing" in microchannels," Applied Physics Letters, vol. 82, No. 3, Jan. 20, 2003.

(56) References Cited

OTHER PUBLICATIONS

Goldschmidt GmbH, "Abil® EM 90 Emulsifier for the formulation of cosmetic W/O creams and lotions," degussa. creating essentials brochure, pp. 1-7, May 2003.
Purnendu K. Dasgupta et al., "Light emitting diode-based detectors Absorbance, fluorescence and spectroelectrochemical measurements in aplanar flow-through cell," Analytica Chimica Acta 500, pp. 337-364, (2003).
R. G. Rutledge et al., "Mathematics of quantitative kinetic PCR and the application of standard curves," Nucleic Acids Research, vol. 31, No. 16, pp. 1-6, (2003).
Chunming Ding et al., "Direct molecular haplotyping of long-range genomic DNA with MI-PCR," PNAS, vol. 100, No. 13, pp. 7449-7453, Jun. 24, 2003.
Devin Dressman et al., "Transforming single DNA molecules into fluorescent magnetic particles for detection and enumeration of genetic variations," PNAS, vol. 100, No. 15, Jul. 22, 2003.
Ulf Landegren et al., "Padlock and proximity probes for in situ and array-based analyses: tools for the post-genomic era," Comp. Funct. Genom, vol. 4, pp. 525-530, (2003).
Gudrun Pohl et al., "Principle and applications of digital PCR" review, www.future-drugs.com, Expert Rev. Mol. Diagn. 4(1), pp. 41-47, (2004).
Groff M. Schroeder et al., "Introduction to Flow Cytometry" version 5.1, 182 pgs. (2004).
Stephane Swillens et al., "Instant evaluation of the absolute initial number Of cDNA copies from a single real-time PCR curve," Nucleic Acids Research, vol. 32, No. 6, pp. 1-6, (2004).
Mats Gullberg et al., "Cytokine detection by antibody-based proximity ligation," PNAS, vol. 101, No. 22, pp. 8420-8424, Jun. 1, 2004.
Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
R. G. Rutledge, "Sigmoidal curve-fitting redefines quantitative realtime PCR with the prospective of developing automated high-throughput applications," Nucleic Acids Research, vol. 32, No. 22, pp. 1-8, (2004).
L. Spencer Roach etal., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).
Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Margaret Macris Kiss et al., "High-Throughput Quantitative Polymerase Chain Reaction in Picoliter Droplets," Analytical Chemistry, 8 pgs., downloaded Nov. 17, 2008.
Jay Shendure et al., "Next-generation DNA sequencing," Nature Biotechnology, vol. 26, No. 10, pp. 1135-1145, Oct. 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.
David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.

Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).
Anthony J. O'Lenick, Jr., "Silicone Emulsions and Surfactants—A Review," Silicone Spectator, Silitech LLC, May 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 4320-4323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Linas Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Micro fluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.
Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Amelia L. Markey et al., "High-throughput droplet PCR," Methods, vol. 50, pp. 277-281, Feb. 2, 2010.
Yoon Sung Nam et al., "Nanosized Emulsions Stabilized by Semisolid Polymer Interphase," Langmuir, ACS Publications, Jul. 23, 2010.
Tatjana Schütze et al., "A streamlined protocol for emulsion polymerase chain reaction and subsequent purification," Analytical Biochemistry, vol. 410, pp. 155-157, Nov. 25, 2010.
Somanath Bhat et al., "Effect of sustained elevated temperature prior to amplification on template copy number estimation using digital polymerase chain reaction," Analyst, vol. 136, pp. 724-732, (2011).
James G. Wetmur, et al., "Linking Emulsion PCR Haplotype Analysis," PCR Protocols, Methods in Molecular Biology, vol. 687, pp. 165-175, (2011).
Paul Vulto et al., "Phaseguides: a paradigm shift in microfluidic priming and emptying," Lab on a Chip, vol. 11, No. 9, pp. 1561-1700, May 7, 2011.
Thinxxs Microtechnology AG, "Emerald Biosystems: Protein Crystallization," 1 pg., downloaded Mar. 8, 2011.
Qun Zhong et al., "Multiplex digital PCR: breaking the one target per color barrier of quantitative PCR," Lab on a Chip, vol. 11, pp. 2167-2174, (2011).
Jiaqi Huang et al., "Rapid Screening of Complex DNA Samples by Single-Molecule Amplification and Sequencing," PLoS One, vol. 6, Issue 5, pp. 1-4, May 2011.
Burcu Kekevi et al., Synthesis and Characterization of Silicone-Based Surfactants as Anti-Foaming Agents, J. Surfact Deterg (2012), vol. 15, pp. 73-81, published online Jul. 7, 2011.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Nicole L. Solimini et al., "Recurrent Hemizygous Deletions in Cancers May Optimize Proliferative Potential," Science, vol. 337, pp. 104-109, Jul. 6, 2012.
Labsmith, "Microfluid Components" webpage, downloaded Jul. 11, 2012.
Labsmith, "CapTite™ Microfluidic Interconnects" webpage, downloaded Jul. 11, 2012.

(56) References Cited

OTHER PUBLICATIONS

Nathan A. Tanner et al., "Simultaneous multiple target detection in real-time loop-mediated isothermal amplification," BioTechniques, vol. 53, pp. 8-19, Aug. 2012.
A. Scherer, California Institute of Technology, "Polymerase Chain Reactors" PowerPoint presentation, 24 pgs., date unknown.
Eschenback Optik GmbH, Optics for Concentrated Photovoltaics (CPV), 1 pg., date unknown.
Anna Musyanovych et al., "Miniemulsion Droplets as Single Molecule Nanoreactors for Polymerase Chain Reaction," Biomacromolecules, vol. 6, No. 4, pp. 1824-1828, (2005).
Max Chabert et al., "Droplet fusion by alternating current (AC) field electrocoalescence in microchannels," Electrophoresis, vol. 26, pp. 3706-3715, (2005).
Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).
Marcel Margulies et al., "Genome sequencing in microfabricated high-density picolitre reactors," Nature, vol. 437, 51 pgs., Sep. 15, 2005.
Kristofer J. Thurecht et al., "Investigation of spontaneous microemulsion formation in supercritical carbon dioxide using high-pressure NMR," Journal of Supercritical Fluids, vol. 38, pp. 111-118, (2006).
Toshko Zhelev et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).
Piotr Garstecki et al., "Formation of droplets and bubbles in a microfluidic T-junction—scaling and mechanism of break-up," Lab on a Chip, vol. 6, pp. 437-446, (2006).
Darren R. Link et al., "Electric Control of Droplets in Microfluidic Devices," Angewandte Chemie Int. Ed., vol. 45, pp. 2556-2560, (2006).
Peter Fielden et al., "Micro-Droplet Technology for High Throughout Systems and Methods," 1 pg., Mar. 8, 2006.
David Emerson et al., "Microfluidic Modelling Activities at C3M," Centre for Microfluidics & Microsystems Modelling, Daresbury Laboratory, pp. 1-26, May 15, 2006.
Richard Williams et al., "Amplification of complex gene libraries by emulsion PCR," Nature Methods, vol. 3, No. 7, pp. 545-550, Jul. 2006.
John H. Leamon et al., "Overview: methods and applications for droplet compartmentalization of biology," Nature Methods, vol. 3, No. 7, pp. 541-543, Jul. 2006.
Andrew D. Griffiths et al., "Miniaturising the laboratory in emulsion droplets," Trends in Biotechnology, vol. 24, No. 9, pp. 395-402, Jul. 14, 2006.
Jian-Bing Fan et al., "Highly parallel genomic assays," Nature Reviews/Genetics, vol. 7, pp. 632-644, Aug. 2006.
Jonas Jarvius et al., "Digital quantification using amplified single-molecule detection," Nature Methods, vol. 3, No. 9, pp. 15 pgs, Sep. 2006.
Kan Liu et al., "Droplet-based synthetic method using microflow focusing and droplet fusion," Microfluid Nanofluid, vol. 3, pp. 239-243, (2007), published online Sep. 22, 2006.
Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.
Kristofer J. Thurecht et al., "Kinetics of Enzymatic Ring-Opening Polymerization of e-Caprolactone in Supercritical Carbon Dioxide," Macromolecules, vol. 39, pp. 7967-7972, (2006).
Machiko Hori et al., "Uniform amplification of multiple DNAs by emulsion PCR," Biochemical and Biophysical Research Communications, vol. 352, pp. 323-328, (2007).
Frank Diehl et al., "Digital quantification of mutant DNA in cancer patients," Current Opinion in Oncology, vol. 19, pp. 36-42, (2007).
Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).
S. Mohr et al., "Numerical and experimental study of a droplet-based PCR chip," Microfluid Nanofluid, vol. 3, pp. 611-621, (2007).
Sigrun M. Gustafsdottir et al., "In vitro analysis of DNA-protein interactions by proximity ligation," PNAS, vol. 104, No. 9, pp. 3067-3072, Feb. 27, 2007.
Daniel J. Diekema et al., "Look before You Leap: Active Surveillance for Multidrug-Resistant Organisms," Healthcare Epidemiology, CID 2007:44, pp. 1101-1107 (Apr. 15), electronically published Mar. 2, 2007.
Charles N. Baroud et al., "Thermocapillary valve for droplet production and sorting," Physical Review E 75, 046302, pp. 046302-1-046302-5, Apr. 5, 2007.
Qinyu Ge et al., "Emulsion PCR-based method to detect Y chromosome microdeletions," Analytical Biochemistry, vol. 367, pp. 173-178, May 10, 2007.
Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.
Y. M. Dennis Lo et al., "Digital PCR for the molecular detection of fetal chromosomal aneuploidy," PNAS, vol. 104, No. 32, pp. 13116-13121, Aug. 7, 2007.
Dayong Jin et al., "Practical Time-Gated Luminescence Flow Cytometry. II: Experimental Evaluation Using UV LED Excitation," Cytometry Part A, 71 A, pp. 797-808, Aug. 24, 2007.
Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.
Nathan Blow, "PCR's next frontier," Nature Methods, vol. 4, No. 10, pp. 869-875, Oct. 2007.
Nicole Pamme, "continuous flow separations in microfluidic devices," Lab on a Chip, vol. 7, pp. 1644-1659, Nov. 2, 2007.
N. Reginald Beer et al., "On-Chip, Real-Time, Single-Coy Polymerase Chain Reaction in Picoliter Droplets," Analytical Chemistry, vol. 79, No. 22, pp. 8471-8475, Nov. 15, 2007.
Yuejun Zhao et al. "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
Sigma-Aldrich, "Synthesis of Mesoporous Materials," Material Matters, 3.1, 17, (2008).
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Shia-Yen Teh et al., "Droplet micro fluidics," Lab on aChip, vol. 8, pp. 198-220, Jan. 11, 2008.
Chloroform (Phenomenex), Solvent Miscibility Table, Internet Archive WayBackMachine, 3 pgs., Feb. 1, 2008.
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Palani Kumaresan et al., "High-Throughput Single Copy DNA Amplification and Cell Analysis in Engineered Nanoliter Droplets," Analytical Chemistry, 17 pgs., Apr. 15, 2008.
Somil C. Mehta et a., "Mechanism of Stabilization of Silicone Oil—Water Emulsions Using Hybrid Siloxane Polymers," Langmuir, vol. 24, No. 9, pp. 4558-4563, Mar. 26, 2008.
Rhutesh K. Shah et al., "Polymers fit for function Making emulsions drop by drop," Materials Today, vol. 11, No. 4, pp. 18-27, Apr. 2008.
Mohamed Abdelgawad et al., "All-terrain droplet actuation," Lab on a Chip, vol. 8, pp. 672-677, Apr. 2, 2008.
Lung-Hsin Hung et al., "Rapid microfabrication of solvent-resistant biocompatible microfluidic devices," Lab on a Chip, vol. 8, pp. 983-987, Apr. 8, 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.

(56) References Cited

OTHER PUBLICATIONS

Vivienne N. Luk et al., "Pluronic Additives: A Solution to Sticky Problems in Digital Microfluidics," Langmuir, vol. 24, No. 12, pp. 6382-6289, May 16, 2008.
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
Simant Dube et al., "Mathematical Analysis of Copy Number Variation in a DNA Sample Using Digital PCR on a Nanofluidic Device," PLoS One, vol. 3, Issue 8, pp. 1-9, Aug. 6, 2008.
Jian Qin et al., "Studying copy number variations using a nano fluidic platform," Nucleic Acids Research, vol. 36, No. 18, pp. 1-8, Aug. 18, 2008.
C. Holtze et al., "Biocompatible surfactants for water-in-fluorocarbon emulsions," Lab on a Chip, vol. 8, pp. 1632-1639, Sep. 2, 2008.

\* cited by examiner

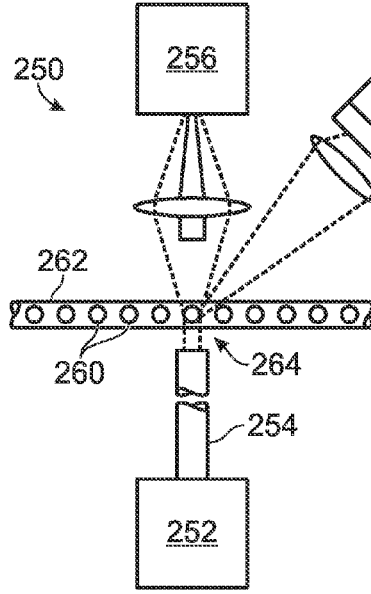
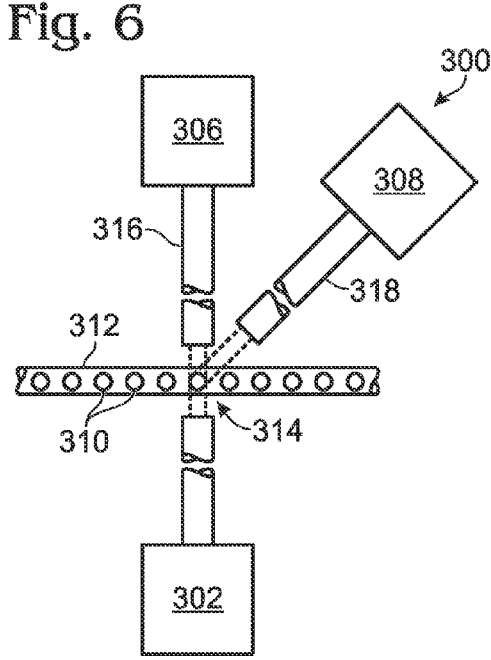
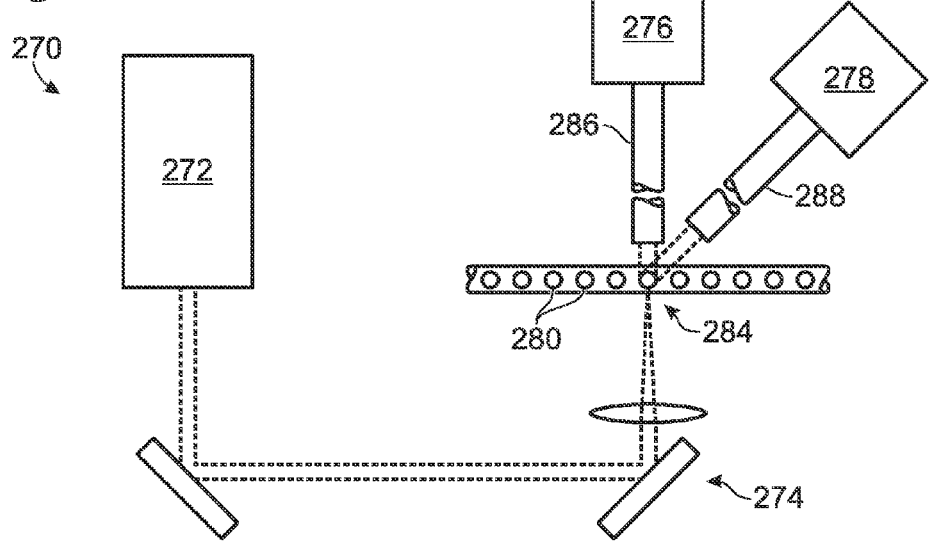

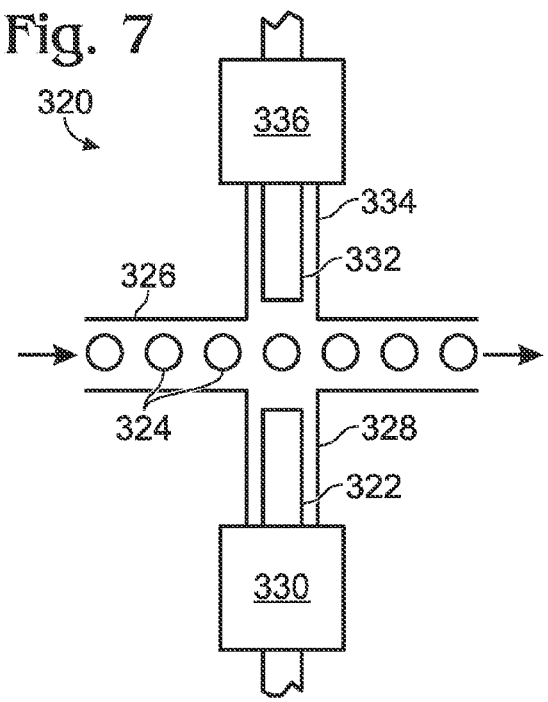
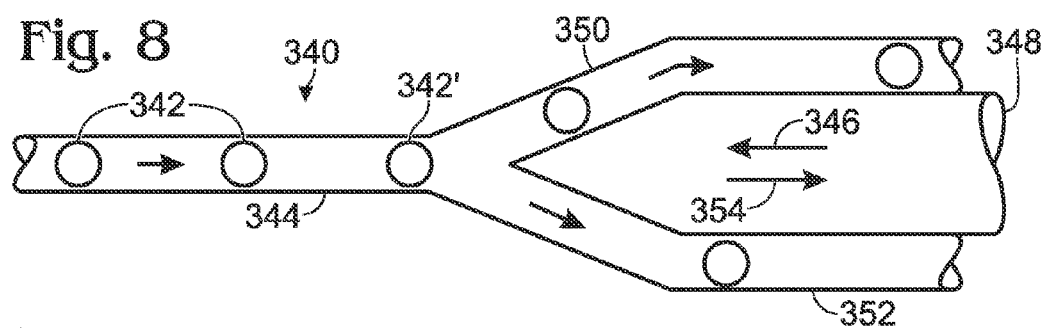
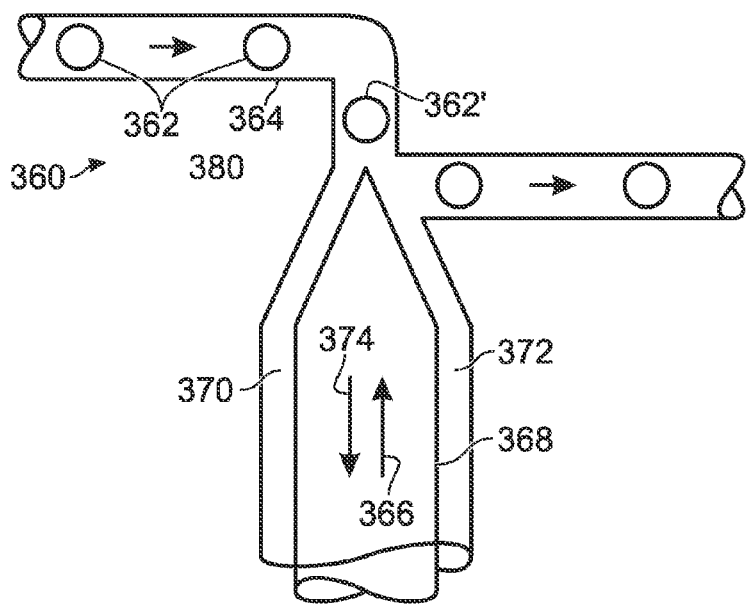

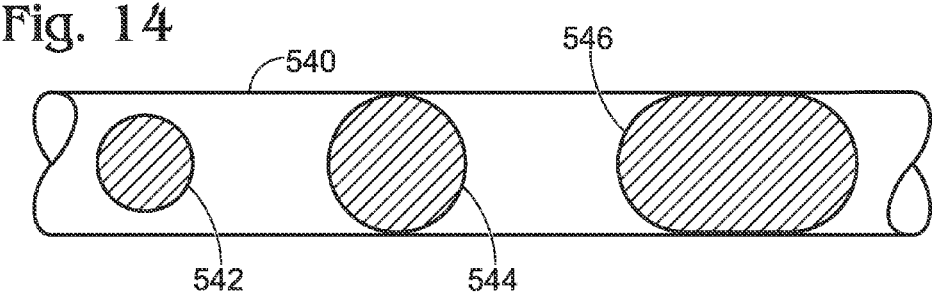
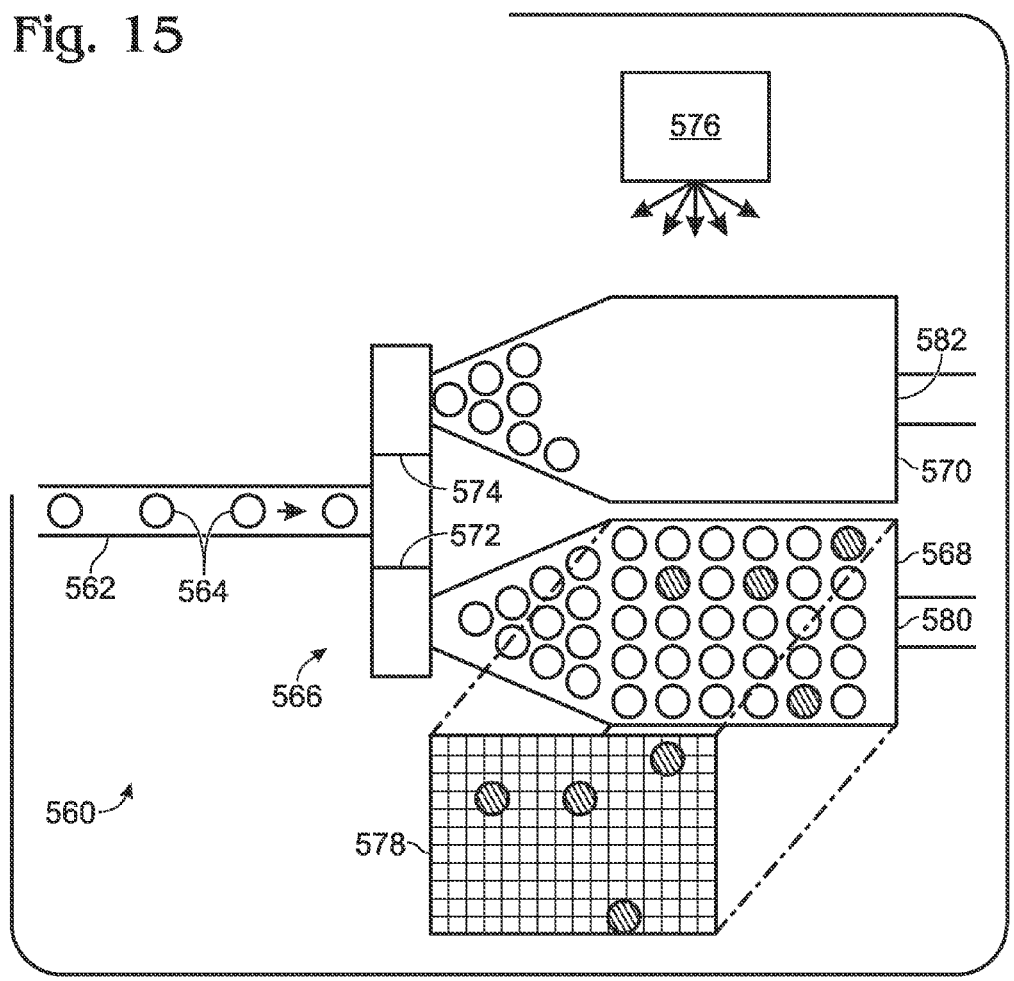

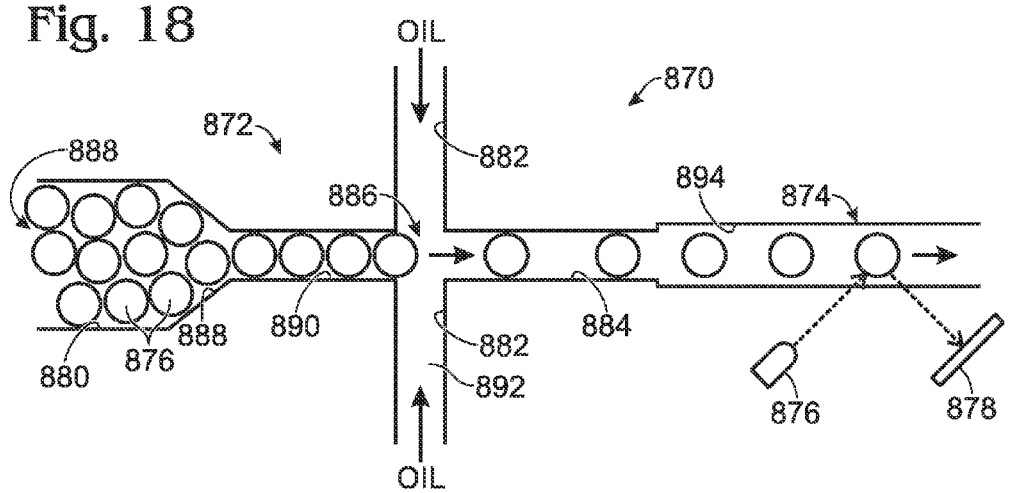
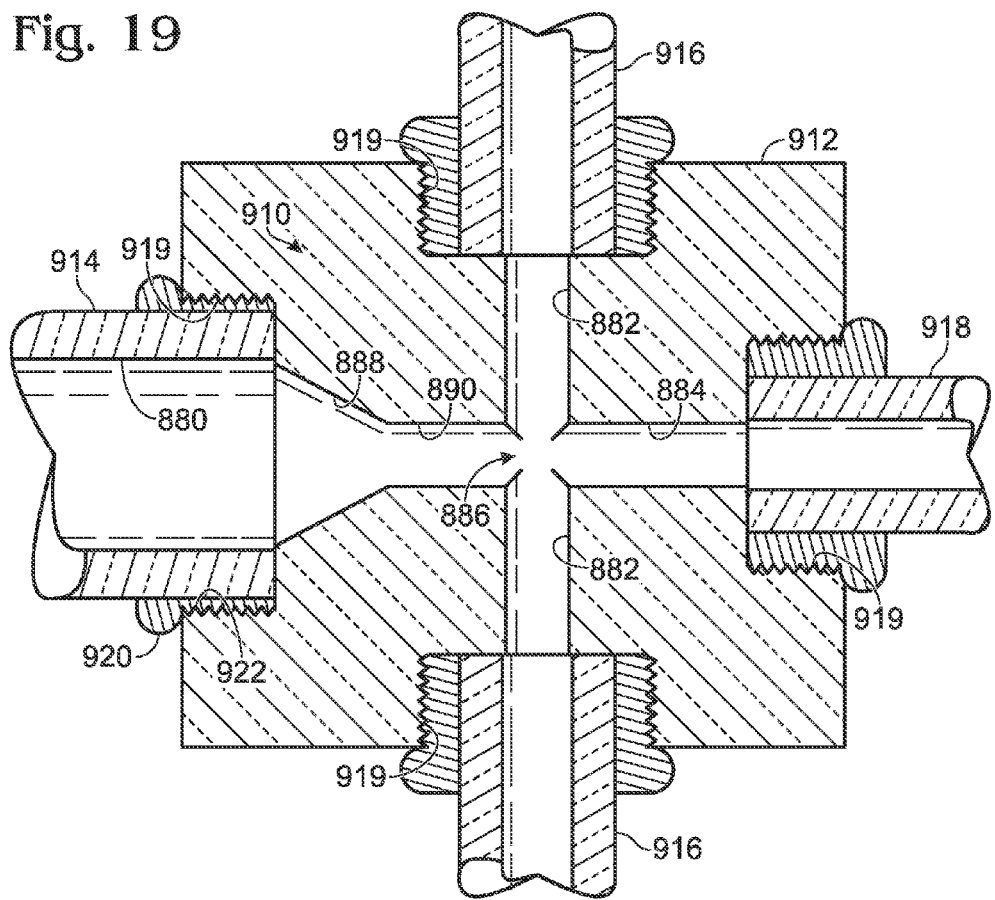

SYSTEM FOR DETECTION OF SPACED DROPLETS

CROSS-REFERENCES TO PRIORITY APPLICATIONS

This application is a continuation-in-part of the following patent applications: Ser. No. 12/586,626, filed Sep. 23, 2009, now U.S. Pat. No. 9,156,010; Ser. No. 12/862,542, filed Aug. 24, 2010, now U.S. Pat. No. 9,194,861; Ser. No. 12/890,550, filed Sep. 24, 2010, now U.S. Pat. No. 8,633,015; Ser. No. 13/245,575, filed Sep. 26, 2011, now abandoned; Ser. No. 13/945,661, filed Jul. 18, 2013; Ser. No. 12/962,507, filed Dec. 7, 2010, now U.S. Pat. No. 9,216,392; Ser. No. 12/962,511, filed Dec. 7, 2010; Ser. No. 12/962,502, filed Dec. 7, 2010, now U.S. Pat. No. 9,248,417; Ser. No. 12/963,523, filed Dec. 8, 2010, now U.S. Pat. No. 9,126,160; Ser. No. 13/039,233, filed Mar. 2, 2011, now U.S. Pat. No. 8,709,762; Ser. No. 12/976,827, filed Dec. 22, 2010; Ser. No. 13/341,669, filed Dec. 30, 2011; Ser. No. 13/341,678, filed Dec. 30, 2011, now U.S. Pat. No. 8,730,479; Ser. No. 13/072,673, filed Mar. 25, 2011, now U.S. Pat. No. 9,132,394; Ser. No. 13/341,688, filed Dec. 30, 2011; Ser. No. 13/287,120, filed Nov. 1, 2011, now U.S. Pat. No. 9,089,844; Ser. No. 13/424,304, filed Mar. 19, 2012, now U.S. Pat. No. 9,222,128; Ser. No. 13/548,062, filed Jul. 12, 2012, now U.S. Pat. No. 8,951,939; Serial No. PCT/US2012/048198, filed Jul. 25, 2012; Ser. No. 13/562,198, filed Jul. 30, 2012, now U.S. Pat. No. 8,663,920; Ser. No. 13/287,095, filed Nov. 1, 2011, now abandoned; and Ser. No. 13/863,231, filed Apr. 15, 2013.

U.S. patent application Ser. No. 12/586,626, in turn, is based upon and claims the benefit under 35 U.S.C. §119(e) of the following U.S. provisional patent applications: Ser. No. 61/194,043, filed Sep. 23, 2008; Ser. No. 61/206,975, filed Feb. 5, 2009; Ser. No. 61/271,538, filed Jul. 21, 2009; Ser. No. 61/275,731, filed Sep. 1, 2009; Ser. No. 61/277,200, filed Sep. 21, 2009; Ser. No. 61/277,203, filed Sep. 21, 2009; Ser. No. 61/277,204, filed Sep. 21, 2009; Ser. No. 61/277,216, filed Sep. 21, 2009; Ser. No. 61/277,249, filed Sep. 21, 2009; and Ser. No. 61/277,270, filed Sep. 22, 2009.

U.S. patent application Ser. No. 12/862,542, in turn, is based upon and claims the benefit under 35 U.S.C. §119(e) of U.S. Provisional Patent Application Ser. No. 61/275,860, filed Sep. 2, 2009.

U.S. patent application Ser. No. 12/890,550, in turn, is a continuation-in-part of U.S. patent application Ser. No. 12/586,626, filed Sep. 23, 2009, which, in turn, claims priority to further applications as listed above.

U.S. patent application Ser. No. 13/245,575, in turn, is a continuation of U.S. patent application Ser. No. 12/586,626, filed Sep. 23, 2009, which, in turn, claims priority to further applications as listed above.

U.S. patent application Ser. No. 13/945,661, in turn, is a continuation-in-part of the following U.S. patent applications: Ser. No. 13/251,016, filed Sep. 30, 2011, now abandoned; Ser. No. 13/245,575, filed Sep. 26, 2011; and Ser. No. 12/976,827, filed Dec. 22, 2010, the latter two of which, in turn, claim priority to further applications as listed elsewhere in this section.

U.S. patent application Ser. No. 12/962,507, in turn, is a continuation of U.S. patent application Ser. No. 12/586,626, filed Sep. 23, 2009, Pub. No. US-2010-0173394-A1, which, in turn, claims priority to further applications as listed above.

U.S. patent application Ser. No. 12/962,511, in turn, is a continuation of U.S. patent application Ser. No. 12/586,626, filed Sep. 23, 2009, Pub. No. US-2010-0173394-A1, which, in turn, claims priority to further applications as listed above.

U.S. patent application Ser. No. 12/962,502, in turn, is a continuation of U.S. patent application Ser. No. 12/586,626, filed Sep 23, 2009, Pub. No. US-2010-0173394-A1, which, in turn, claims priority to further applications as listed above.

U.S. patent application Ser. No. 12/963,523, in turn, is a continuation of U.S. patent application Ser. No. 12/586,626, filed Sep. 23, 2009, Pub. No. US-2010-0173394-A1, which, in turn, claims priority to further applications as listed above.

U.S. patent application Ser. No. 13/039,233, in turn, is based upon and claims the benefit under 35 U.S.C. §119(e) of U.S. Provisional Patent Application Ser. No. 61/309,837, filed Mar. 2, 2010.

U.S. patent application Ser. No. 12/976,827, in turn, is based upon and claims the benefit under 35 U.S.C. §119(e) of the following U.S. provisional patent applications: Ser. No. 61/309,845, filed Mar. 2, 2010; Ser. No. 61/341,218, filed Mar. 25, 2010; Ser. No. 61/317,635, filed Mar. 25, 2010; Ser. No. 61/380,981, filed Sep. 8, 2010; Ser. No. 61/409,106, filed Nov. 1, 2010; Ser. No. 61/409,473, filed Nov. 2, 2010; Ser. No. 61/410,769, filed Nov. 5, 2010; and Ser. No. 61/417,241, filed Nov. 25, 2010.

U.S. patent application Ser. No. 13/341,669, in turn, is a continuation of PCT Patent Application Serial No. PCT/US2011/030101, filed Mar. 25, 2011, which, in turn, is based upon and claims the benefit under 35 U.S.C. §119(e) of U.S. Provisional Patent Application Ser. No. 61/341,218, filed Mar. 25, 2010.

U.S. patent application Ser. No. 13/341,678, in turn, is a continuation of PCT Patent Application Serial No. PCT/US2011/030077, filed Mar. 25, 2011, which, in turn, claims the benefit under 35 U.S.C. §119(e) of U.S. Provisional Patent Application Ser. No. 61/317,684, filed Mar. 25, 2010.

U.S. patent application Ser. No. 13/072,673, in turn, is based upon and claims the benefit under 35 U.S.C. §119(e) of U.S. Provisional Patent Application Ser. No. 61/317,635, filed Mar. 25, 2010, and U.S. Provisional Patent Application Ser. No. 61/467,347, filed Mar. 24, 2011, and is a continuation-in-part of U.S. patent application Ser. No. 12/586,626, filed Sep. 23, 2009, Pub. No. US-2010-0173394-A1, which, in turn, claims priority to further applications as listed above.

U.S. patent application Ser. No. 13/341,688, in turn, is a continuation of PCT Patent Application Serial No. PCT/US2011/030097, filed Mar. 25, 2011, which, in turn, claims the benefit under 35 U.S.C. §119(e) of the following U.S. provisional patent applications: Ser. No. 61/341,065, filed Mar. 25, 2010; and Ser. No. 61/467,347, filed Mar. 24, 2011.

U.S. patent application Ser. No. 13/287,120, in turn, is based upon and claims the benefit under 35 U.S.C. §119(e) of the following U.S. provisional patent applications: Ser. No. 61/409,106, filed Nov. 1, 2010; Ser. No. 61/409,473, filed Nov. 2, 2010; Ser. No. 61/410,769, filed Nov. 5, 2010.

U.S. patent application Ser. No. 13/424,304, in turn, is based upon and claims the benefit under 35 U.S.C. §119(e) of U.S. Provisional Patent Application Ser. No. 61/454,373, filed Mar. 18, 2011.

U.S. patent application Ser. No. 13/548,062, in turn, is based upon and claims the benefit under 35 U.S.C. §119(e)

of the following U.S. provisional patent applications: Ser. No. 61/507,082, filed Jul. 12, 2011; and Ser. No. 61/510,013, filed Jul. 20, 2011.

PCT Patent Application Serial No. PCT/US2012/048198, in turn, is based upon and claims the benefit under 35 U.S.C. §119(e) of U.S. Provisional Patent Application Ser. No. 61/511,445, filed Jul. 25, 2011.

U.S. patent application Ser. No. 13/562,198, in turn, is based upon and claims the benefit under 35 U.S.C. §119(e) of the following U.S. provisional patent applications: Ser. No. 61/513,474, filed Jul. 29, 2011; and Ser. No. 61/601,514, filed Feb. 21, 2012.

U.S. patent application Ser. No. 13/287,095, in turn, is continuation-in-part of U.S. patent application Ser. No. 12/976,827, filed Dec. 22, 2010, which, in turn, claims priority to further applications as listed above.

U.S. patent application Ser. No. 13/863,231, in turn, is based upon and claims the benefit under 35 U.S.C. §119(e) of U.S. Provisional Patent Application Ser. No. 61/624,199, filed Apr. 13, 2012.

Each of these priority documents is incorporated herein by reference in its entirety for all purposes.

CROSS-REFERENCES TO MATERIALS INCORPORATED BY REFERENCE

This application incorporates by reference in its entirety for all purposes U.S. Pat. No. 7,041,481, issued May 9, 2006.

This application incorporates by reference in their entireties for all purposes the following U.S. patent applications: Ser. No. 12/586,626, filed Sep. 23, 2009; Ser. No. 12/862,542, filed Aug. 24, 2010; Ser. No. 12/890,550, filed Sep. 24, 2010; Ser. No. 12/962,502, filed Dec. 7, 2010; Ser. No. 12/962,507, filed Dec. 7, 2010; Ser. No. 12/962,511, filed Dec. 7, 2010; Ser. No. 12/963,523, filed Dec. 8, 2010; Ser. No. 12/976,827, filed Dec. 22, 2010; Ser. No. 13/039,233, filed Mar. 2, 2011; Ser. No. 13/072,673, filed Mar. 25, 2011; Ser. No. 13/245,575, filed Sep. 26, 2011; Ser. No. 13/250,815, filed Sep. 30, 2011; Ser. No. 13/251,016, filed Sep. 30, 2011; Ser. No. 13/287,095, filed Nov. 1, 2011; Ser. No. 13/287,120, filed Nov. 1, 2011; Ser. No. 13/341,669, filed Dec. 30, 2011; Ser. No. 13/341,678, filed Dec. 30, 2011; Ser. No. 13/341,688, filed Dec. 30, 2011; Ser. No. 13/424,304, filed Mar. 19, 2012; Ser. No. 13/548,062, filed Jul. 12, 2012; Ser. No. 13/549,360, filed Jul. 13, 2012; Ser. No. 13/562,198, filed Jul. 30, 2012; Ser. No. 13/603,235, filed Sep. 4, 2012; Ser. No. 13/863,231, filed Apr. 15, 2013; Ser. No. 13/945,661, filed Jul. 18, 2013; Ser. No. 13/949,115, filed Jul. 23, 2013; Ser. No. 13/973,940, filed Aug. 22, 2013; Ser. No. 14/032,149, filed Sep. 19, 2013; Ser. No. 14/054,698, filed Oct. 15, 2013; and Ser. No. 14/099,750, filed Dec. 6, 2013.

This application incorporates by reference in their entireties for all purposes the following PCT patent applications: Ser. No. PCT/US2011/030077, filed Mar. 25, 2011; Serial No. PCT/US2011/030097, filed Mar. 25, 2011; Ser. No. PCT/US2011/030101, filed Mar. 25, 2011; and Serial No. PCT/US2012/048198, filed Jul. 25, 2012.

This application incorporates by reference in their entireties for all purposes the following U.S. provisional patent applications: Ser. No. 61/194,043, filed Sep. 23, 2008; Ser. No. 61/206,975, filed Feb. 5, 2009; Ser. No. 61/271,538, filed Jul. 21, 2009; Ser. No. 61/275,731, filed Sep. 1, 2009; Ser. No. 61/275,860, filed Sep. 2, 2009; Ser. No. 61/277,200, filed Sep. 21, 2009; Ser. No. 61/277,203, filed Sep. 21, 2009; Ser. No. 61/277,204, filed Sep. 21, 2009; Ser. No. 61/277,216, filed Sep. 21, 2009; Ser. No. 61/277,249, filed Sep. 21, 2009; Ser. No. 61/277,270, filed Sep. 22, 2009; Ser. No. 61/309,837, filed Mar. 2, 2010; Ser. No. 61/309,845, filed Mar. 2, 2010; Ser. No. 61/317,635, filed Mar. 25, 2010; Ser. No. 61/317,684, filed Mar. 25, 2010; Ser. No. 61/341,065, filed Mar. 25, 2010; Ser. No. 61/341,218, filed Mar. 25, 2010; Ser. No. 61/380,981, filed Sep. 8, 2010; Ser. No. 61/409,106, filed Nov. 1, 2010; Ser. No. 61/409,473, filed Nov. 2, 2010; Ser. No. 61/410,769, filed Nov. 5, 2010; Ser. No. 61/417,241, filed Nov. 25, 2010; Ser. No. 61/454,373, filed Mar. 18, 2011; Ser. No. 61/467,347, filed Mar. 24, 2011; Ser. No. 61/507,560, filed Jul. 13, 2011; Ser. No. 61/507,082, filed Jul. 12, 2011; Ser. No. 61/510,013, filed Jul. 20, 2011; Ser. No. 61/511,445, filed Jul. 25, 2011; Ser. No. 61/513,474, filed Jul. 29, 2011; Ser. No. 61/530,340, filed Sep. 1, 2011; Ser. No. 61/601,514, filed Feb. 21, 2012; Ser. No. 61/624,199, filed Apr. 13, 2012; Ser. No. 61/674,516, filed Jul. 23, 2012; Ser. No. 61/692,635, filed Aug. 23, 2012; Ser. No. 61/703,200, filed Sep. 19, 2012; Ser. No. 61/714,033, filed Oct. 15, 2012; Ser. No. 61/734,296, filed Dec. 6, 2012; Ser. No. 61/759,775, filed Feb. 1, 2013;

This application incorporates by reference in its entirety for all purposes Joseph R. Lakowicz, PRINCIPLES OF FLUORESCENCE SPECTROSCOPY ($2^{nd}$ Ed. 1999).

INTRODUCTION

Many biomedical applications rely on high-throughput assays of samples combined with reagents. For example, in research and clinical applications, high-throughput genetic tests using target-specific reagents can provide high-quality information about samples for drug discovery, biomarker discovery, and clinical diagnostics, among others. As another example, infectious disease detection often requires screening a sample for multiple genetic targets to generate high-confidence results.

The trend is toward reduced volumes and detection of more targets. However, creating and mixing smaller volumes can require more complex instrumentation, which increases cost. Accordingly, improved technology is needed to permit testing greater numbers of samples and combinations of samples and reagents, at a higher speed, a lower cost, and/or with reduced instrument complexity.

Emulsions hold substantial promise for revolutionizing high-throughput assays. Emulsification techniques can create billions of aqueous droplets that function as independent reaction chambers for biochemical reactions. For example, an aqueous sample (e.g., 200 microliters) can be partitioned into droplets (e.g., four million droplets of 50 picoliters each) to allow individual sub-components (e.g., cells, nucleic acids, proteins) to be manipulated, processed, and studied discretely in a massively high-throughput manner.

Splitting a sample into droplets offers numerous advantages. Small reaction volumes (picoliters to nanoliters) can be utilized, allowing earlier detection by increasing reaction rates and forming more concentrated products. Also, a much greater number of independent measurements (thousands to millions) can be made on the sample, when compared to conventional bulk volume reactions performed on a micoliter scale. Thus, the sample can be analyzed more accurately (i.e., more repetitions of the same test) and in greater depth (i.e., a greater number of different tests). In addition, small reaction volumes use less reagent, thereby lowering the cost per test of consumables. Furthermore, microfluidic technology can provide control over processes used for the generation, mixing, incubation, splitting, sorting, and detection of droplets, to attain repeatable droplet-based measurements.

Aqueous droplets can be suspended in oil to create a water-in-oil emulsion (W/O). The emulsion can be stabilized with a surfactant to reduce or prevent coalescence of droplets during heating, cooling, and transport, thereby enabling thermal cycling to be performed. Accordingly, emulsions have been used to perform single-copy amplification of nuclei acid target molecules in droplets using the polymerase chain reaction (PCR).

Compartmentalization of single molecules of a nucleic acid target in droplets of an emulsion alleviates problems encountered in amplification of larger sample volumes. In particular, droplets can promote more efficient and uniform amplification of targets from samples containing complex heterogeneous nucleic acid populations, because sample complexity in each droplet is reduced. The impact of factors that lead to biasing in bulk amplification, such as amplification efficiency, G+C content, and amplicon annealing, can be minimized by droplet compartmentalization. Unbiased amplification can be critical in detection of rare species, such as pathogens or cancer cells, the presence of which could be masked by a high concentration of background species in complex clinical samples.

Despite their allure, emulsion-based assays present technical challenges for high-throughput testing. As an example, the arrangement and packing density of droplets may need to be changed during an assay, such as after the droplets have been reacted and before detection. In particular, it may be advantageous to thermally cycle droplets at a high packing density in a batch mode. However, detection of signals from closely packed droplets may be problematic because the signals cannot always be correctly assigned to individual droplets. Thus, there is a need for systems that space droplets from one another after reaction and before detection for improved detection accuracy.

SUMMARY

The present disclosure provides a system, including methods and apparatus, for detection of spaced droplets.

BRIEF DESCRIPTION OF THE DRAWINGS

FIG. 4 is a schematic depiction of an optical detection system in which stimulating radiation is transferred toward sample-containing droplets through an optical fiber, in accordance with aspects of the present disclosure.

FIG. 5 is a schematic depiction of an optical detection system in which scattered and fluorescence radiation are transferred away from sample-containing droplets through optical fibers, in accordance with aspects of the present disclosure.

FIG. 6 is a schematic depiction of an optical detection system in which stimulating radiation is transferred toward sample-containing droplets through an optical fiber and in which scattered and fluorescence radiation are transferred away from the droplets through optical fibers, in accordance with aspects of the present disclosure.

FIG. 7 depicts an intersection region where incident radiation intersects with sample-containing droplets traveling through a fluid channel, illustrating how optical fibers may be integrated with sections of fluidic tubing.

FIG. 8 depicts another intersection region where incident radiation intersects with sample-containing droplets traveling through a fluid channel, illustrating how a single optical fiber may be used to transmit both incident radiation and stimulated fluorescence.

FIG. 9 depicts another intersection region configured to transmit both incident radiation and stimulated fluorescence through a single optical fiber, and also configured to transfer radiation to and from substantially one droplet at a time.

FIG. 14 depicts a section of fluidic tubing, illustrating how an appropriate choice of fluid channel diameter can facilitate proper spacing between droplets, in accordance with aspects of the present disclosure.

FIG. 15 depicts a batch fluorescence detection system, in accordance with aspects of the present disclosure.

FIG. 18 is a schematic view of an exemplary detection system including a cross-shaped spacer positioned upstream of an examination region where light is detected from droplets, in accordance with aspects of the present disclosure.

FIG. 19 is a sectional view of another exemplary cross-shaped spacer that may be included in the detection system of FIG. 18, in accordance with aspects of the present disclosure.

DETAILED DESCRIPTION

The present disclosure provides a system, including methods and apparatus, for detection of spaced droplets. The system particularly involves a droplet spacer that increases the average distance between droplets, and that optionally arranges droplets in single file in a flow stream that is upstream of an examination region in a flow path, to permit serial detection of individual, spaced droplets passing through the examination region.

A detection system for droplet-based assays is provided. The system may comprise a tip and a channel network. The channel network may define a flow path for droplets, with the flow path extending from the tip, through a confluence region configured to increase an average distance between droplets, and through an examination region disposed downstream of the confluence region. The system also may comprise a detector operatively connected to the examination region. The flow path may have a minimum diameter adjacent the confluence region.

A method of detection for droplet-based assays is provided. Droplets may be driven along a flow path from a tip, through a confluence region where a dilution fluid is introduced into the flow path, and through an examination region disposed downstream of the confluence region. Light may be detected from the examination region as droplets pass through. The flow path may have a minimum diameter adjacent the confluence region.

Figure 1:
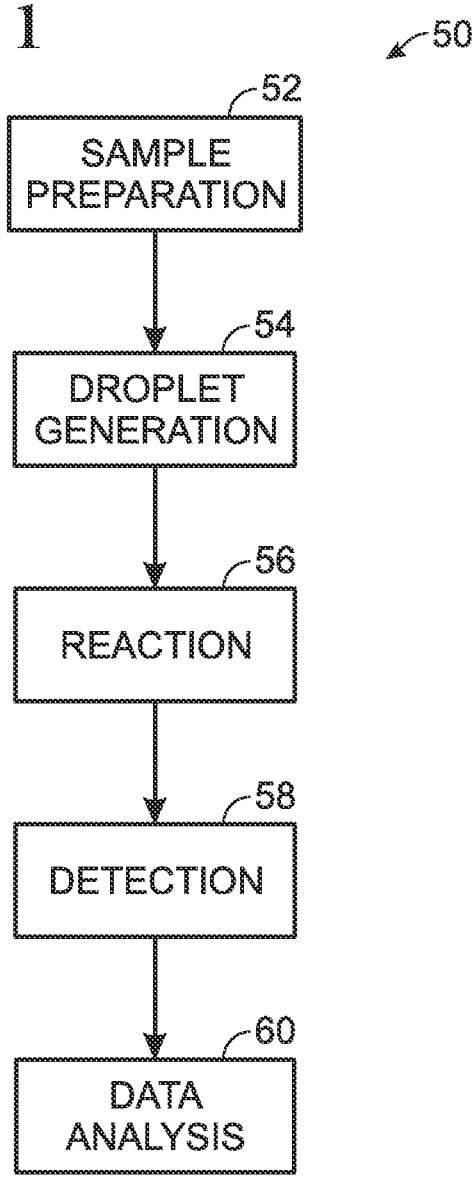
FIG. 1 is a flowchart listing exemplary steps that may be performed in a method of sample analysis using droplets and droplet-based assays, in accordance with aspects of the present disclosure.

FIG. 1 shows an exemplary system 50 for performing a droplet-, or partition-, based assay. In brief, the system may include sample preparation 52, droplet generation 54, reaction 56 (e.g., amplification), detection 58, and data analysis 60. The system may be utilized to perform a digital PCR (polymerase chain reaction) analysis. More specifically, sample preparation 52 may involve collecting a sample, such as a clinical or environmental sample, treating the sample to release an analyte (e.g., a nucleic acid or protein, among others), and forming a reaction mixture involving the analyte (e.g., for amplification of a target nucleic acid that corresponds to the analyte or that is generated in a reaction (e.g., a ligation reaction) dependent on the analyte). Droplet generation 54 may involve encapsulating the analyte and/or target nucleic acid in droplets, for example, with an average of about one copy of each analyte and/or target nucleic acid per droplet, where the droplets are suspended in an immiscible carrier fluid, such as oil, to form an emulsion. Reaction 56 may involve subjecting the droplets to a suitable reaction, such as thermal cycling to induce PCR amplification, so that target nucleic acids, if any, within the droplets are amplified to form additional copies. Detection 58 may involve detecting some signal(s) from the droplets indicative of whether or not there was amplification. Finally, data analysis 60 may involve estimating a concentration of the analyte and/or target nucleic acid in the sample based on the percentage of droplets in which amplification occurred.

These and other aspects of the system are described in further detail below, particularly with respect to exemplary detection systems and/or droplet spacers, and in the patent documents listed above under Cross-References and incorporated herein by reference.

I. Detection System Overview

The present disclosure describes exemplary detection systems, for example, for detecting sample-containing droplets. The systems may involve sensing or detecting the droplets themselves and/or contents of the droplets. The detection of droplets themselves may include determining the presence or absence of a droplet (or a plurality of droplets) and/or a characteristic(s) of the droplet, such as its size (e.g., radius or volume), shape, type, and/or aggregation state, among others. The detection of the contents of droplets may include determining the nature of the contents (e.g., whether or not the droplet contains a sample(s)) and/or a characteristic of the contents (e.g., whether or not the contents have undergone a reaction, such as PCR, the extent of any such reaction, etc.).

The detection of droplets and their contents, if both are detected, may be performed independently or coordinately, in any suitable order. For example, the detection may be performed serially (one droplet at a time), in parallel, in batch, and so forth.

The detection of droplets and their contents may be performed using any technique(s) or mechanism(s) capable of yielding, or being processed to yield, the desired information. These mechanisms may include optical techniques (e.g., absorbance, transmission, reflection, scattering, birefringence, dichroism, fluorescence, phosphorescence, etc.), electrical techniques (e.g., capacitance), and/or acoustic techniques (e.g., ultrasound), among others. The fluorescence techniques, in turn, may include fluorescence intensity, fluorescence polarization (or fluorescence anisotropy) (FP), fluorescence correlation spectroscopy (FCS), fluorescence recovery after photobleaching (FRAP), total internal reflection fluorescence (TIRF), fluorescence resonance energy transfer (FRET), fluorescence lifetime, and/or fluorescence imaging, among others.

The present disclosure describes exemplary detection systems, including droplet sensors and reaction sensors. In these exemplary systems, the droplet sensor may generate and detect scattered light, and the reaction sensor may generate and detect fluorescence, among other approaches. These systems are described, for convenience, in the context of a PCR reaction; however, the techniques apply more generally to any reaction, such as a biochemical reaction, capable of generating, or being modified to generate, a detectable signal.

In an exemplary PCR assay (or other nucleic acid amplification assay), the sample is first combined with reagents in a droplet, and the droplet is then thermocycled to induce PCR. It may then be desirable to measure the fluorescence of the droplets to determine which, if any, contained one or more target nucleotide sequences. This generally involves illuminating the droplets with radiation at a wavelength chosen to induce fluorescence, or a change in a characteristic of the fluorescence, from one or more fluorescent probes associated with the amplified PCR target sequence(s). For example, in an exemplary fluorescence intensity assay, if a relatively large intensity of fluorescence is detected, this indicates that PCR amplification of the target nucleotide occurred in the droplet, and thus that the target was present in that portion of the sample. Conversely, if no fluorescence or a relatively small intensity of fluorescence is detected, this indicates that PCR amplification of the target nucleotide did not occur in the droplet, and thus that a target was likely not present in that portion of the sample. In other fluorescence-based embodiments, the extent of reaction could be determined from a decrease in fluorescence intensity, instead of a decrease, and/or a change in one or more other fluorescence parameters, including polarization, energy transfer, and/or lifetime, among others.

II. Droplet Spacer Overview

The present disclosure describes exemplary droplet spacers, also termed singulators or separators, that may be positioned in a flow path of a detection system and/or droplet transport system. A spacer may be disposed at any suitable position, such as in fluid communication with and upstream of an examination region (e.g., an irradiation zone), in fluid communication with and downstream of an incubation/reaction site (e.g., a thermal cycling region), or both, among others. The spacer may increase or decrease the average distance between droplets in a flow stream, may rearrange the droplets from a multiple file to a single file arrangement, and/or may focus droplets within the flow stream.

The droplet spacer may include at least two inlet channels, an outlet channel, and a confluence region or separation region forming a junction between the inlet channels and the outlet channel. The at least two inlet channels may include a droplet inlet channel that receives an emulsion of droplets in a continuous phase, and at least one carrier or dilution channel that receives a carrier fluid, such as an oil, for diluting the droplets/emulsion. The carrier fluid received in the dilution channel may be the same as, or a different carrier fluid from, that in which the droplets are disposed in the droplet inlet channel.

The spacer may have any suitable configuration. For example, the inlet channels and the outlet channel collectively may form a T, a cross, a coaxial arrangement, or the like.

The droplet inlet channel may have a uniform diameter or may taper toward the confluence region. If tapered, the droplet inlet channel may have a maximum diameter that is greater than that of the droplets (e.g., at least about 50%, 100%, 150%, 200%, or 300% greater in diameter, among others). The droplet inlet channel may taper to a minimum diameter (e.g., adjacent the confluence region) that is about the same or less than the diameter of the droplets. For example, the diameter of the droplet inlet channel may be between about 90% and about 100% of an average diameter of the droplets, among others. The use of a minimum diameter that is about the same or less than the diameter of the droplets may permit only one droplet to enter the confluence region at a time, thereby facilitating production of a single-file stream of droplets for a downstream detection site.

The dilution inlet channel (or channels) may have a diameter that is less than, about the same as, or greater than the maximum or minimum diameter of the droplet inlet channel. The spacer may have any suitable number of dilution channels, such as one, two, three, or more. The dilution channel(s) thus may be disposed on only side of the confluence region, on opposing sides, on three or more sides, etc. In some examples, the dilution channel may communicate with the confluence region circumferentially.

The confluence region may have any suitable structure. The confluence region may have a diameter that is greater than the minimum diameter of the droplet inlet channel and greater than the diameter of the droplets. As a result, any droplets newly-formed at the droplet spacer (such as by fragmentation of a coalesced set of droplets) should be larger than the original droplets of interest. Accordingly, any droplets detected to be larger than a threshold size by a downstream detector (and thus likely to be formed after thermal cycling) may be excluded from the analysis. The confluence region may taper toward the outlet channel, which may act to accelerate each individual droplet out of the confluence region. Furthermore, the droplet inlet channel and the droplet outlet channel may be near one another, such as separated by no more than about twice, one, or one-half the droplet diameter, to promote exit of droplets from the confluence region, thereby allowing only one droplet to be present in the confluence region at a time.

The spacer may define a minimum diameter along a flow path followed by droplets between a pick-up tip and an examination region. Accordingly, the spacer may provide a maximum resistance to fluid flow along the flow path. Fluid may be driven along the flow path at a sufficient velocity to provide a high shear, to help prevent clogs and remove particulates. The high shear also may help to increase the distance between droplets.

Further aspects of transport systems/detection systems involving spacers are described below in Examples 4 and 7-11.

III. Examples

The following examples describe specific exemplary detection systems and spacers, in accordance with aspects of the invention. Additional pertinent disclosure may be found in the patent documents listed above under Cross-References and incorporated herein by reference, particularly Ser. No. 61/277,203, filed Sep. 21, 2009; U.S. Provisional Patent Application Ser. No. 61/317,635, filed Mar. 25, 2010; U.S. Provisional Patent Application Ser. No. 61/467,347, filed Mar. 24, 2011; and U.S. patent application Ser. No. 12/586,626, filed Sep. 23, 2009, Pub. No. US-2010-0173394-A1.

EXAMPLE 1

Detection System 1

This example describes an optical detection system based on measuring the end-point fluorescence signal of each sample/reagent droplet after a PCR amplification process is complete. The exemplary system is suitable for making both qualitative and quantitative measurements; see FIGS. 2 and 3.

Figure 2:
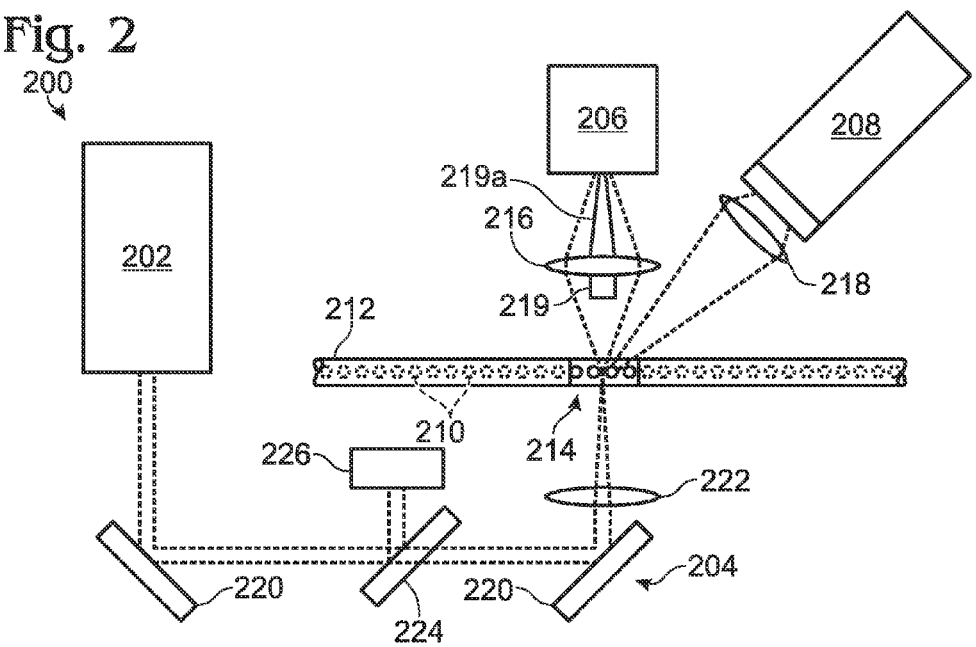
FIG. 2 is a schematic depiction of an optical detection system for irradiating sample-containing droplets and detecting fluorescence subsequently emitted by the droplets, in accordance with aspects of the present disclosure.

FIG. 2 depicts a detection system 200 configured to detect both scattered and fluorescence radiation. Detection system 200 includes a radiation source 202, transmission optics generally indicated at 204, a forward scatter detector 206, and a fluorescence detector 208. The forward scatter detector may be replaced or augmented, in some embodiments, by side and/or back scatter detectors, among others, configured to detect light detected to the side or back of the sample, respectively. Similarly, the fluorescence detector may be replaced or augmented, in some embodiments, by an epi-fluorescence detector, among others, configured to detect fluorescence emitted anti-parallel to the excitation light (e.g., back toward transmission optics 204 (which could, in such embodiments, include a dichroic or multi-dichroic beam splitter and suitable excitation and emission filters)).

Sample-containing droplets 210, which have already undergone at least some degree of PCR thermocycling, are transferred through a capillary tube or other similar fluid channel 212, which intersects the path of radiation from radiation source 202 at an intersection region generally indicated at 214. An optical element 216, such as a converging lens, may be placed between intersection region 214 and forward scatter detector 206, to focus scattered radiation on the scatter detector. Similarly, an optical element 218 may be placed between intersection region 214 and fluorescence detector 208, to focus fluorescence radiation on the fluorescence detector. The system may include an obscuration bar 219, operatively positioned between the sample and detector, which reduces the amount of direct (unscattered) excitation radiation (light) that falls on the detector. The obscuration bar, shown here as a small square object in front of optical element 216, may create a triangular-shaped shadow 219a behind the optical element. This arrangement makes it easier for detector 206 to detect changes in index of refraction that have scattered (at small angles) the normal beam.

Radiation from source 202 may be partially scattered when it encounters a droplet, and the scattered radiation may be used to determine one or more properties of the droplet. For example, scattered radiation indicating the presence of a droplet in intersection region 214 may be sensed by scatter detector 206, and this information may be used to activate fluorescence detector 208, which may otherwise remain deactivated (i.e., when a droplet is not present in the intersection region) to conserve power within the system. Even if the fluorescence detector remains continuously active, detecting the presence of a droplet may be useful for other purposes. For example, tracking the droplets passing through intersection region 214 may be desirable because some droplets passing through the intersection region may not be detected by the fluorescence detector (e.g., if the droplets do not contain reaction product). In addition, tracking the droplets may allow background noise (i.e., the signal received by the detector in the absence of a droplet) to be removed, improving the signal-to-noise ratio. Furthermore, as described below, various properties of a detected droplet may be estimated from data sensed by forward or side scatter detector 206.

Radiation detected by scatter detector 206 may be used to infer the size (or other properties) of a detected droplet. Specifically, a measurement of the duration of a scattering event representing the presence of a droplet within intersection region 214, in conjunction with knowledge of the average speed of droplet passage through the intersection region, can be used to determine the width of the droplet in a plane normal to the direction of the incident radiation from source 202. If this width is less than the diameter of channel 214, then it can be inferred that the droplet is an approximate sphere with a diameter less than the diameter of channel 214, and the volume of the droplet can be calculated. If, on the other hand, the width of the droplet exceeds the diameter of channel 214, this indicates that the droplet is likely contacting the walls of the channel and is not spherical. However, the droplet volume still may be estimated by modeling the droplet as a cylinder or other similar shape passing through the channel. As described below, a determination of droplet volume may be useful for normalizing the results of any corresponding fluorescence detection.

In some cases, radiation from source 202 also may be scattered from intersection region 214 even if it does not encounter a droplet, for instance, if it encounters a partially reflective surface such as a fluid interface or a wall of fluid channel 212. This type of scattered radiation will generally have a different signature than radiation scattered from a droplet, so that it generally serves merely as a background for droplet scattering events. Whether scattering occurs in the absence of a droplet depends on the particular configuration of system 200, as will be described below. Similarly, scattering may occur when droplets outside a desired size range pass through the intersection region, and the signature of radiation scattered from such droplets may be used to affect the subsequent treatment of such droplets. For example, the fluorescence signals received from unusually small or large droplets may be removed from a statistical sample, to increase statistical accuracy. In any case, after passing through intersection region 214, scattered and/or unscattered radiation from radiation source 202 is directed toward forward scatter detector 206.

Radiation from source 202 that is absorbed by droplets within intersection region 214 may stimulate the emission of fluorescence radiation that can be detected by fluorescence detector 208. More specifically, radiation intersecting a droplet may excite a fluorescent probe, such as a TAQMAN probe, that is configured to fluoresce significantly only if the fluorescent portion of the probe becomes separated from a quencher molecule. This separation, or cleaving, typically occurs only when polymerase replicates a sequence to which the probe is bound. In other words, a probe will fluoresce significantly only in droplets within which a target nucleotide sequence has been amplified through PCR. Accordingly, radiation source 202 will generally be configured to emit radiation at a wavelength that stimulates fluorescent emission from one or more probes known to be present in the sample, and fluorescence detector 208 will be configured to detect such stimulated radiation.

Radiation source 202 may take any form suitable for transmitting radiation at one or more desired wavelengths or wavelength bands. For example, radiation source 202 may be a laser, such as a diode laser, emitting substantially monochromatic light at a wavelength of 488 nanometers (nm) or at some other desired wavelength. Radiation source 202 also may include multiple separate lasers, emitting light at either a single wavelength or at multiple different wavelengths. One or more (or all) of the lasers of radiation source 202 may be replaced by an alternate source of light, such as a light-emitting diode (LED) configured to emit a directed beam of radiation at one or more desired wavelengths. In yet other embodiments, white light illumination, for example, from a Halogen lamp, may also be used to provide the radiation source.

Transmission optics 204 may include any optical components suitable for directing, focusing, or otherwise desirably affecting radiation from source 202. For example, as depicted in FIG. 2, the transmission optics may include one or more steering mirrors 220, each configured to direct incident radiation in a desired direction such as toward another optical component or toward intersection region 214. Also as depicted in FIG. 2, the transmission optics may include a converging lens 222, which is configured to focus radiation from source 202 onto intersection region 214 to maximize scattering and fluorescence caused by the radiation. The transmission optics may further include additional components such as aperture stops, filters, diverging lenses, shaped mirrors, and the like, to affect the transmission path and/or properties of the radiation from source 202 before it arrives at intersection region 214. In addition, the transmission optics further may include (in this and other embodiments) a mechanism for monitoring properties of the incident (excitation) radiation. For example, the transmission optics may include a partial mirror 224 for reflecting a portion of the incident radiation to a detector 226, such as a photodiode, for monitoring the intensity of the incident light. This would allow correction of the detected scattering and fluorescence for changes that simply reflect changes in the intensity of the incident light.

Forward scatter detector 206 is configured to receive and detect radiation scattered from droplets passing through intersection region 214, as described previously. Various types of detectors may be suitable, depending on the desired cost and/or sensitivity of the detector. In approximate order of decreasing sensitivity, exemplary types of scatter detectors that may be suitable include photodiodes, avalanche photodiodes, multi-pixel photon counters, and photomultiplier tubes. The presence of optical element 216, which typically will be a converging lens used to refocus scattered radiation toward scatter detector 206, may decrease the necessary sensitivity of the forward scatter detector for a given application, by increasing the intensity per unit area of scattered radiation incident on the detector.

Fluorescence detector 208 is configured to receive and detect fluorescence radiation emitted by droplets at or near the time they pass through intersection region 214. Various types of fluorescence detectors may be suitable, depending on factors such as desired cost and/or sensitivity, including photodiodes, avalanche photodiodes, multi-pixel photon counters, and photomultiplier tubes. Also as in the case of the forward scatter, utilizing an optical element 218, typically a converging lens, between intersection region 214 and fluorescence detector 208 may decrease the necessary sensitivity of the fluorescence detector by increasing the intensity per unit area of fluorescence radiation incident on the detector.

Figure 3:
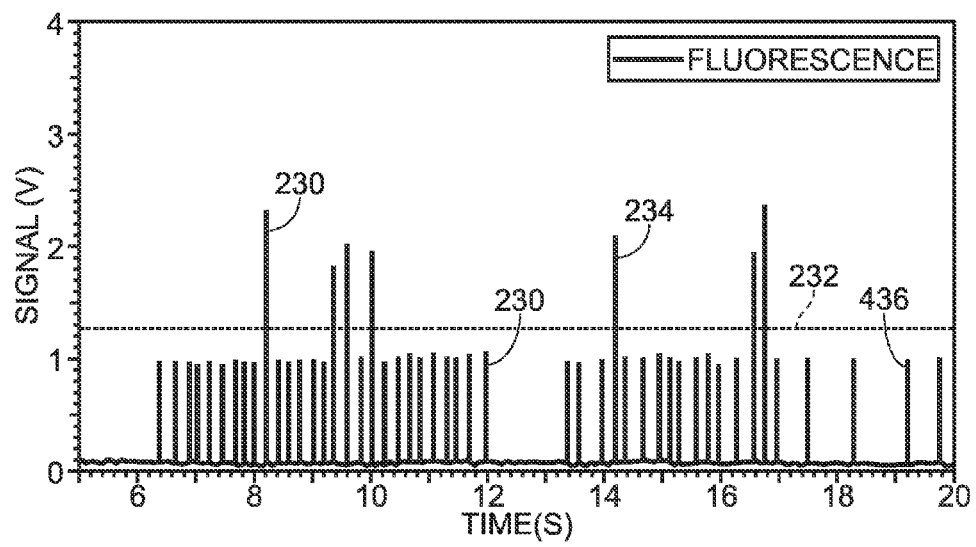
FIG. 3 is a graph of intensity versus time for fluorescence detected by an optical detection system such as the system of FIG. 2, illustrating the distinction between fluorescence emitted by droplets containing a target and droplets not containing a target.

FIG. 3 depicts exemplary fluorescence measurements made by fluorescence detector 208. More specifically, FIG. 3 shows a post-PCR end-point fluorescence trace from droplets, in which each "peak" 230 represents the intensity of detected fluorescence emitted by an individual droplet flowing through intersection region 214. As FIG. 3 indicates, the resulting histogram can be used to identify positive from negative signals. Specifically, the signals depicted in FIG. 3 each may be compared to a cut-off or threshold fluorescence level, as indicated by dashed line 232. Signals exceeding the threshold level will be interpreted as positive for PCR amplification, and thus for the presence of the target nucleotide sequence in the corresponding droplet, as indicated for an exemplary signal at 234. On the other hand, signals falling below threshold level 232 will be interpreted as negative outcomes, indicating that the corresponding droplet did not contain the target.

An example of a negative signal is indicated at 236, where the detection of a sub-threshold amount of fluorescence is due to the presence of uncleaved fluorescent probe in the droplet. As described previously, the fluorescence of such probes is generally not completely quenched even in the absence of cleavage by a binding polymerase. Also, the differences in fluorescent intensity of a positive, as seen in the signal voltage peak heights between the positive peak at 230 and positive peak 234, can be attributed to different amounts of starting nucleic acid target originally in the droplet prior to PCR (e.g., one versus two starting targets). The ratio of different amounts of starting target amounts may be governed by Poisson statistics.

Typically, hundreds to millions of droplets are analyzed per run. In any case, after a desired number of signals have been detected by fluorescence detector 208, i.e., after a desired number of droplets have passed through intersection region 214, the positive and negative signals are counted and analyzed. Analysis is typically performed using receiver-operator characteristic curves and Poisson statistics to determine target presence and target concentration, respectively. Running analysis using Poisson statistics can also be performed to give an estimate of target concentration prior to processing all the droplets (i.e., subsets of the total droplets are used in the statistical analysis). The analysis of droplets is further described in U.S. patent application Ser. No. 12/586,626, filed Sep. 23, 2009, Pub. No. US-2010-0173394-A1, which is incorporated herein by reference.

EXAMPLE 2

Detection Systems Using Optical Fibers

This example describes fluorescence detectors configured to measure the end-point fluorescence signal of sample/reagent droplet after PCR, and which utilize one or more optical fibers to transmit radiation to and/or from an intersection region within which illuminating radiation intersects the path of the sample-containing droplets. The exemplary systems are suitable for making both qualitative and quantitative measurements; see FIGS. 4-9.

FIG. 4 depicts an optical detection system, generally indicated at 250, which is similar to system 200 depicted in FIG. 2 except that transmission optics 204 of system 200 have been replaced by an optical fiber 254. Optical fiber 254 may be constructed from a glass, a plastic, and/or any other material that is substantially transparent to radiation of one or more particular desired wavelengths and configured to transmit that radiation along the length of the fiber, preferably with little or no loss of intensity.

Replacing the transmission optics with optical fiber 254 may allow system 250 to be constructed relatively inexpensively and in a more space-saving manner than systems using optical elements such as mirrors and lenses. This results from the fact that the cost and space associated with the other optical elements is no longer necessary, and also from the fact that optical fiber 254 may be shaped in any desired manner, allowing significant design flexibility. Aside from optical fiber 254, detection system 250 otherwise includes a radiation source 252, a forward scatter detector 256, and a fluorescence detector 258, all of which are similar to their counterparts in system 200 and will not be described again in detail.

Optical fiber 254 is depicted in FIG. 4 as ending a short distance from droplets 260 traveling in fluid channel 262 through an intersection region generally indicated at 264, in which radiation emitted from the end of the optical fiber intersects with the droplets traveling through the fluid channel. Other configurations are possible in which, for example, the optical fiber is configured to focus radiation more precisely toward the intersection region and/or is integrated directly into the fluid channel. These possibilities are described below in more detail; see FIGS. 7-9 and accompanying discussion.

FIG. 5 depicts an optical detection system, generally indicated at 270, which is similar to system 200 depicted in FIG. 2 except that optical elements 216 and 218 of system 200 have been replaced by optical fibers 286 and 288 in system 270 of FIG. 5. As in the case of optical fiber 254 shown in FIG. 4 and described above, optical fibers 286 and 288 each may be constructed from a glass, a plastic, and/or any other material that is substantially transparent to radiation of one or more particular desired wavelengths and configured to transmit that radiation along the length of the fiber, preferably with little or no loss of intensity.

In the case of system 270, optical fiber 286 will be configured to transmit at least scattered radiation having a wavelength equal to the wavelength of light emitted by radiation source 272 (which generally does not change during scattering), and optical fiber 288 will be configured to transmit at least fluorescence radiation emitted by any fluorescent probes within droplets 280 that are excited by incident radiation from source 272. Accordingly, optical fibers 286 and 288 may in some cases be constructed from different materials. The use of optical fibers 286 and 288 may result in cost and space savings for the same reasons described previously with respect to the use of optical fiber 254 in system 250.

Aside from the use of optical fibers 286 and 288, system 270 is similar to system 200, including radiation source 272, transmission optics 274, a forward scatter detector 276, and a fluorescence detector 278, which are similar to their previously described counterparts and will not be described further. Radiation from source 272 passes through transmission optics 274 and encounters droplets 280 traveling through fluid channel 282, at an intersection region 284. Some of the forward scattered radiation is transmitted through optical fiber 286 to forward scatter detector 276. Similarly, some of the fluorescence radiation emitted from droplets 280 is transmitted through optical fiber 288 to fluorescence detector 278. As in the case of optical fiber 254 in FIG. 4, optical fibers 286 and 288 are shown starting at a distance from fluid channel 282, but as noted above, other configurations are possible and will be described below with reference to FIGS. 7-9.

FIG. 6 depicts an optical detection system, generally indicated at 300, in which optical fibers are used to transmit both incident and outgoing radiation. More specifically, system 300 includes a radiation source 302, an optical fiber 304 for transmitting emitted radiation away from source 302, a forward scatter detector 306, and a fluorescence detector 308. Post-PCR sample-containing droplets 310 are transferred through fluid channel 312 toward intersection region 314. Optical fiber 316 transmits scattered radiation from intersection region 314 to forward scatter detector 306, and optical fiber 318 transmits fluorescence radiation from intersection region 314 to fluorescence detector 308.

As described previously, the use of optical fibers may result in various cost and space savings. These savings may be further amplified, relative to systems 250 and 270, by the use of fiber optics for all of the radiation transfer in system 300. Aside from the use of optical fibers for radiation transfer and any associated efficiencies, system 300 is similar in both its components and its operation to the previously described systems, and accordingly will not be described further.

FIG. 7 shows a magnified view of an intersection region, generally indicated at 320, in which incident radiation from a radiation source (not shown) is transmitted through an optical fiber 322 to intersect with sample-containing droplets 324 traveling through a droplet input fluid channel 326. Intersection region 320 differs from the intersection regions described previously in that optical fiber 322 is integrated into a radiation input fluid channel 328 that is fluidically connected with fluid channel 326. Thus, radiation is emitted from optical fiber 322 directly into the fluid within the connected fluid channels, so that it encounters droplets 324 without crossing either an interface between air and the fluid channel material (typically some form of glass) or an interface between the fluid channel material and the fluid within the channel.

By configuring the intersection region in this manner and avoiding two interfaces between media with different indices of refraction, undesirable reflections of the incident radiation may be decreased, resulting in a greater intensity of radiation reaching droplets 324. Furthermore, embedding optical fiber 322 within a connected fluid channel may allow for more convenient and stable placement of the optical fiber at a small distance from fluid channel 326 and at a desired orientation relative to fluid channel 326, again potentially resulting in a greater intensity of radiation reaching the droplets. To secure optical fiber 322 in place within channel 328, a fluidic fitting 330 may be placed at an end of channel 328, and configured so that optical fiber 322 passes through an aperture of the fitting in a fluid tight manner.

Intersection regions of the type depicted in FIG. 7 may take various forms. For example, as depicted in FIG. 7, optical fiber 322 may have a slightly smaller outer diameter than the inner diameter of fluid channel 328. Alternatively, optical fiber 322 may have an outer diameter approximately equal to the inner diameter of fluid channel 328, which may lead to an even more secure placement of the optical fiber within the fluid channel. In addition, FIG. 7 depicts an outgoing optical fiber 332 disposed within a fluid channel 334 that is also fluidically connected with fluid channel 326. Optical fiber 332, which is secured within channel 334 by a fluidic fitting 336, is configured to transmit scattered radiation to a forward scatter detector (not shown). In some embodiments, one of incoming optical fiber 322 and outgoing optical fiber 332 may be used, but not the other. Furthermore, one or more additional optical fibers, such as an outgoing optical fiber leading to a fluorescence detector (not shown) may be fluidically coupled into intersection region 320.

FIG. 8 depicts another intersection region, generally indicated at 340, between sample-containing droplets 342 traveling through a fluid channel 344 and excitation radiation 346 emitted from a radiation source (not shown). Excitation radiation 346 is transmitted to intersection region 340 through an optical fiber 348, which is oriented with its long axis parallel to fluid channel 344. As depicted in FIG. 8, optical fiber 348 may come to a point or otherwise be tapered in the region proximal to fluid channel 344, to focus excitation radiation 346 (through internal reflections within the optical fiber) into channel 344 and toward droplets 342. This may allow the excitation radiation to be directed primarily at a single droplet 342', despite the collinear disposition of optical fiber 348 with multiple droplets.

Fluid channel 344, which is configured to transport the droplets to intersection region 340 where the droplets encounter stimulating radiation transmitted by optical fiber 348, is shown splitting into two (or more) outgoing fluid channels 350 and 352 after droplets 342 pass through the central part of intersection region 340. This allows the sample-containing droplets to continue their motion through the PCR system while still allowing a collinear arrangement of fluid channel 344 and optical fiber 348. As FIG. 8 illustrates, the outgoing fluid channels and the optical fiber may be given complementary shapes, so that the optical fiber fits snugly between outgoing channels 350 and 352. This may lead to a relatively stable collinear configuration of the optical fiber and fluid channel 344 (to help self-align the fiber and channel).

The intersection region shown in FIG. 8 is configured so that optical fiber 348 transmits both excitation radiation 346 and also fluorescence radiation 354 emitted by the droplets. The fluorescence radiation is then transmitted back through the optical fiber and toward a fluorescence detector (not shown), which may be integrated with a radiation source into a single component. Due to the shape of the proximal end of optical fiber 348, emitted fluorescence radiation from stimulated droplet 342' may enter optical fiber 348 both "head on" and also from a subsequent position along one side of the optical fiber. This effectively lengthens the integration time of the fluorescence detection, resulting in better detection with a given detector sensitivity.

FIG. 9 depicts another intersection region, generally indicated at 360, which is similar in some respects to intersection region 340 of FIG. 8. Specifically, an optical fiber 368 in FIG. 9 is configured to transmit excitation radiation 366 from a radiation source (not shown) toward sample containing droplets 362 traveling in a fluid channel 364, and fluorescence radiation 374 from an excited droplet 362' back through the optical fiber and toward a fluorescence detector (not shown). Unlike intersection region 340, however, fluid channel 364 of intersection region 360 is oriented mostly perpendicular to the long axis of optical fiber 368, except for a "dog leg" or side-facing region 380 in the central portion of intersection region 360.

Side-facing region 380 of intersection region 360, which is configured to transport the droplets to intersection region 360 where the droplets encounter stimulating radiation transmitted by optical fiber 368, is configured to allow only a small number of droplets, such as one droplet at a time, to travel parallel to the long axis of optical fiber 368. This configuration may result in relatively more accurate detection of fluorescence radiation, because only one droplet (or a small number of droplets) is stimulated with incident radiation at a time, and only the stimulated droplet(s) emits substantial fluorescence radiation back into optical fiber 368 for detection.

Optical fiber 368 of FIG. 9 may be partially or completely surrounded by fluid, and this surrounding fluid may be in fluid communication with fluid channel 364. However, unlike fluid channels 350 and 352 of FIG. 8, fluid regions 370 and 372 surrounding optical fiber 368, which may in some cases constitute a single continuous fluid region, are too small to allow passage of any sample-containing droplets. Rather, these surrounding fluid region(s) are configured primarily to remove unnecessary interfaces between the optical fiber and the droplets, increasing the intensity of the incident radiation as described previously.

EXAMPLE 3

Detection Systems with Plural Radiation Channels

In some cases, a detection system according to the present disclosure may include multiple separate incident radiation channels to illuminate sample-containing droplets that have undergone PCR thermocycling. This example describes two such systems and some of their potential uses; see FIGS. 10 and 11.

Figure 10:
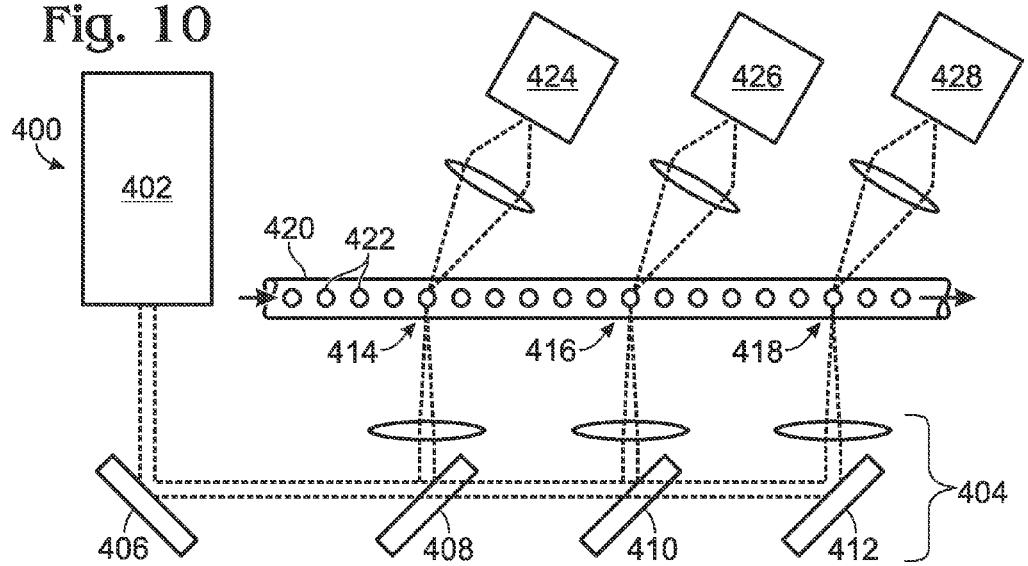
FIG. 10 is a schematic depiction of an optical detection system in which the incident radiation is split into a plurality of separate beams, in accordance with aspects of the present disclosure.

FIG. 10 depicts a multi-channel cytometry-type optical detection system, generally indicated at 400. Detection system 400 includes a radiation source 402, configured to emit radiation at one or more desired wavelengths. As described previously, a radiation source according to the present disclosure may be of various types, such as an LED source or a laser source, and may emit radiation substantially at a single wavelength, at a plurality of substantially discrete wavelengths, or within one or more ranges of wavelengths.

Radiation from source 402 passes from the source toward transmission optics, as generally indicated at 404. Transmission optics 404 may include one or more optical elements, such as a mirror 406, configured primarily to redirect radiation emitted by source 402 in a desired direction. Transmission optics 404 also may include one or more optical elements, such as reflective elements 408, 410, 412, configured to split the radiation emitted by source 402 into several different portions, each of which may be redirected in a particular manner, such as the manner shown in FIG. 10. Alternatively, radiation source 402 may be omitted, and reflective elements 408, 410, 412 each may be replaced by a separate radiation source. In some cases, providing plural radiation sources in this manner may be simpler than splitting the radiation from a single source.

In some instances, reflective elements 408, 410, 412 may be configured to transmit and reflect incident radiation in different ways. For example, reflective element 408 may be configured to reflect approximately one-third of the radiation incident upon it and to transmit approximately two-thirds of the radiation incident upon it, reflective element 410 may be configured to reflect approximately one-half of the radiation incident upon it and to transmit approximately one-half of the radiation incident upon it, and reflective element 412 may be configured to reflect substantially all of the radiation incident upon it. In this manner, radiation emitted by radiation source 402 may be split into three portions of approximately equal intensity.

In cases where it is desirable to split the radiation emitted by source 402 into a number of channels other than three, a plurality of reflective surfaces may be configured appropriately. Specifically, when n channels are desired, n reflective elements may be used, with the first reflective element configured to reflect fraction 1/n and to transmit fraction (n−1)/n of the radiation incident upon it, the second reflective element configured to reflect fraction 1/(n−1) and to transmit fraction (n−2)/(n−1) of the radiation incident upon it, the third reflective element configured to reflect fraction 1/(n−2) and to transmit fraction (n−3)/(n−2) of the radiation incident upon it, and so forth, until the last reflective element in the sequence is a pure mirror that reflects all of the radiation incident upon it and transmits none. This results in each of the n reflective elements reflecting an equal fraction 1/n of the radiation emitted by the radiation source.

An arrangement configured to split radiation from a source into several portions of either approximately equal intensity or differing intensities may be useful, for example, when it is desirable to search for various targets, each of which is bound to a fluorescent probe configured to be excited by the same wavelength of incident radiation but to fluoresce at a different wavelength. For instance, reflective surfaces 408, 410 and 412 may be configured to reflect radiation toward intersection regions 414, 416 and 418, respectively, which may be viewed as different adjacent portions of a single, larger intersection region. Similarly, when a plurality of radiation sources are used instead of reflective surfaces, each radiation source may be configured to transmit fluorescence stimulating radiation to a different adjacent portion of the intersection region.

In the intersection region(s), the arriving radiation will intersect a fluid channel 420 (such as a capillary tube) through which sample-containing droplets 422 are moving. Each droplet thus may be irradiated a plurality of times, and accordingly may be stimulated to emit fluorescence radiation a plurality of times if the irradiated droplet contains any of several desired target nucleic acid sequences. However, the droplet may emit a different wavelength of stimulated radiation depending upon which target it contains (and thus which fluorescent probe has been cleaved from its associated quenching molecule by replication of the target).

To detect stimulated fluorescence radiation corresponding to the various targets, a plurality of fluorescence detectors 424, 426, 428 may be used, with each detector positioned and oriented to receive fluorescence radiation produced at a different one of intersection regions 414, 416, 418 (or at a different portion of the larger intersection region encompassing regions 414, 416, 418). Furthermore, each fluorescence detector may be configured to detect fluorescence at a different wavelength, corresponding to one or more (but not all) of the varieties of target molecules or target nucleic acid sequences. Thus, a given irradiated droplet may emit stimulated fluorescence that is detected by just one of detectors 424, 426, 428, resulting in a "positive" detection of just one (or a subset) of the target sequences. In this manner, system 400 may be used to search for multiple targets simultaneously.

Splitting incident radiation in the manner of system 400 also may be useful when it is desirable to illuminate sample-containing droplets for more time than it takes the droplet to pass through the unsplit beam of the source. For instance, as described above, system 400 may be configured so that droplets 422 passing through a fluid channel 420 intersect radiation from source 402 at several intersection regions 414, 416, 418 corresponding to the various split beams. If these intersection regions are disposed relatively near each other, then each droplet may essentially be continuously illuminated in an area spanning all of the intersection regions 414, 416, 418. The resulting relatively long integration time (i.e., the time of exposure of a droplet to illuminating radiation) may result in greater fluorescence from each target-containing droplet, and thus in greater accuracy of the detection system. Another way to obtain a similar result is illustrated in FIG. 11 and will be described in detail below.

Still considering FIG. 10, detection system 400 also may be used to search for multiple different nucleic acid targets in cases where various probes that respond to different incident wavelengths of excitation radiation have been combined with a sample. For example, radiation source 402 may be configured to emit radiation at a plurality of discrete wavelengths or wavelength ranges, by using a plurality of radiation emitters or a single emitter configured to produce radiation at all of the desired wavelengths. In this case, each of reflective surfaces 408 and 410 (and possibly 412) may be dichroic and configured to reflect substantially all of the radiation at a particular wavelength (or within a particular wavelength range) and to transmit the remaining incident radiation. Alternatively, as described above, a plurality of radiation sources may be provided and configured to transmit fluorescence stimulating radiation at a different wavelength.

When dichroic reflective surfaces are provided, reflective surface 408 may be configured to reflect a particular wavelength or wavelength range toward intersection region 414, reflective surface 410 may be configured to reflect another particular wavelength or wavelength range toward intersection region 416, and reflective surface 412 may be configured to reflect yet another particular wavelength or wavelength range toward intersection region 418. Alternatively, reflective surface 412 may be configured to reflect all radiation toward region 418, since this will include any desired radiation that was not already reflected by surfaces 408 and 410. Accordingly, different wavelengths of incident radiation will arrive at each intersection region 414, 416, 418, and stimulated fluorescence emission will occur only if a probe sensitive to a particular arriving wavelength has been activated due to polymerase cleaving of its associated quenching molecule, i.e., only if a particular target is present. Detectors 424, 426, 428 may be used to monitor the activation of droplets within the various intersection regions, as described previously.

Figure 11:
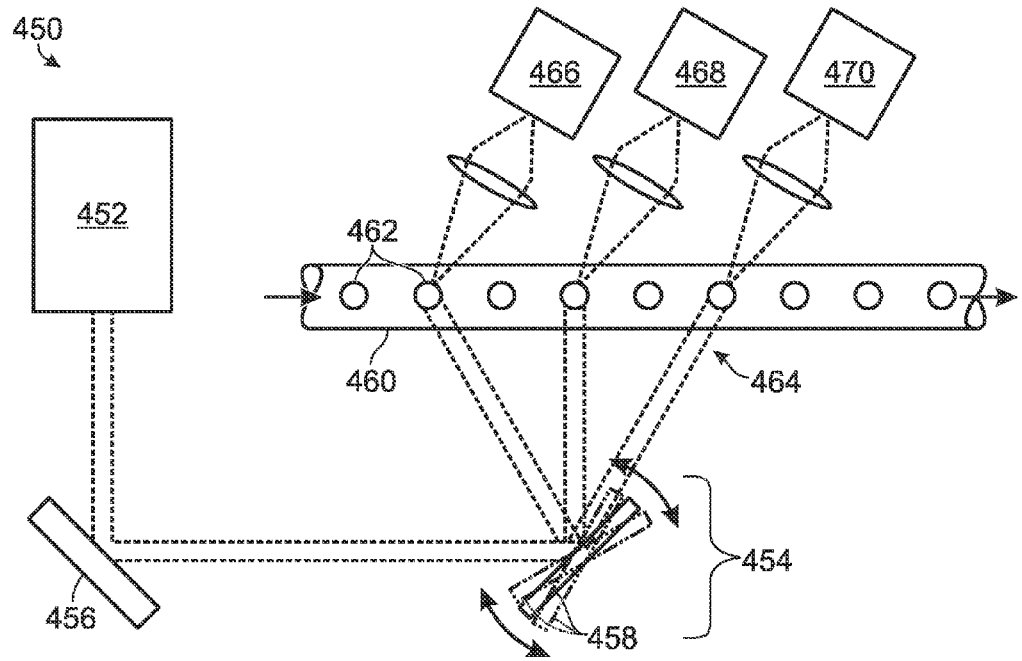
FIG. 11 is a schematic depiction of an optical detection system in which the incident radiation is spread by an adjustable mirror into a relatively wide intersection region, in accordance with aspects of the present disclosure.

FIG. 11 depicts another multi-channel cytometry-type optical detection system, generally indicated at 450. System 450 is generally similar to system 400, including a radiation source 452 and transmission optics generally indicated at 454. In the case of system 450, the transmission optics may include first and second mirrors 456, 458 configured to redirect radiation emitted by source 452 in a desired manner. Transmission optics 454 also may include one or more other optical elements (not shown) for focusing radiation from source 452, as described previously.

As indicated in FIG. 11, mirror 458 may be adjustable so that it is configured to reflect radiation at a range of different angles, to direct it toward a range of different positions along a fluid channel 460 through which sample-containing droplets 462 are being transferred. Thus, the reflected radiation defines an intersection region, generally indicated at 464, which is substantially wider than it would be if mirror 458 was fixed in a single orientation. If mirror 458 is adjusted relatively rapidly, this configuration may allow radiation from source 452 to illuminate more than one droplet at a time, or may cause a single droplet to fluoresce at various positions within fluid channel 460. In this case, a plurality of detectors 466, 468, 470 may be oriented to look for radiation at particular wavelengths corresponding to various target probes.

Alternatively, if the adjustment speed of mirror 458 is chosen to correspond to the known approximate speed of sample-containing droplets traveling within fluid channel 460, then the mirror may effectively increase the illumination time of each droplet by "tracking" the droplet through the channel. In this case, it may be appropriate to use only a single fluorescence detector, with a field of view that spans the entire path traveled by a droplet during its illumination.

EXAMPLE 4

Separation of Droplets

Figure 13:
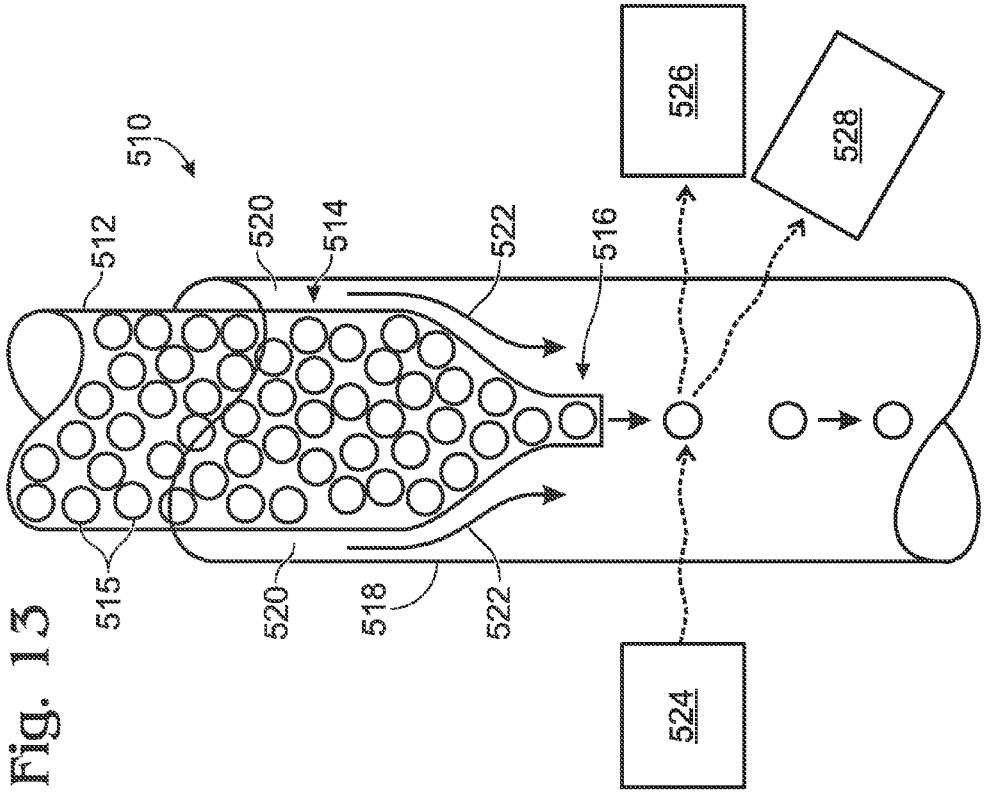
FIG. 13 depicts another flow focus mechanism for separating sample-containing droplets from each other by a desired distance, in accordance with aspects of the present disclosure.
Figure 12:
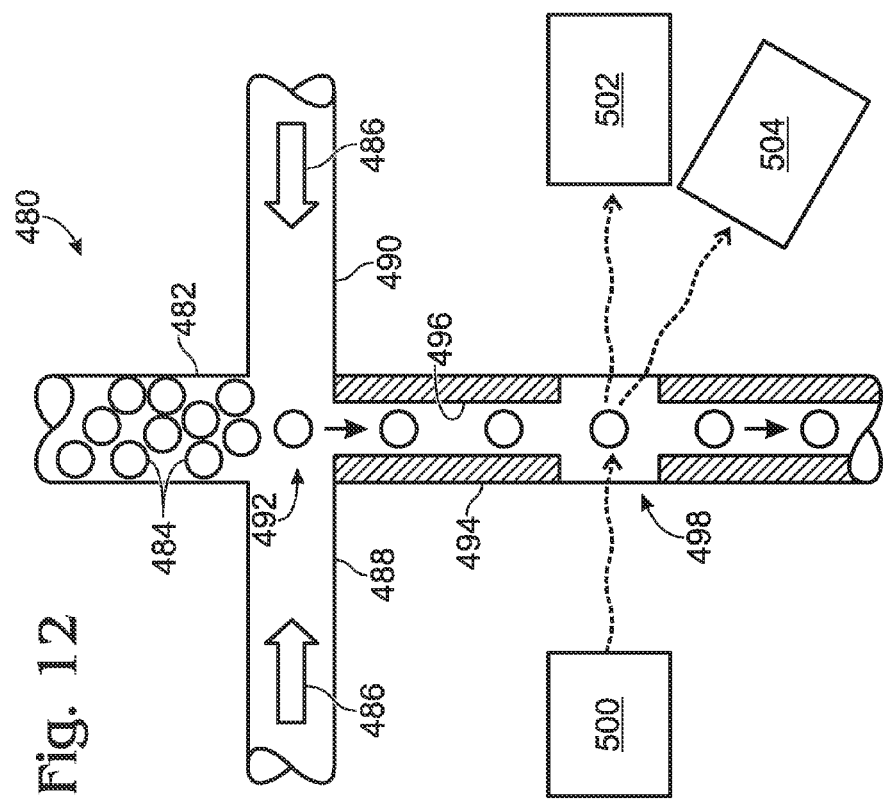
FIG. 12 depicts a flow focus mechanism for separating sample-containing droplets from each other by a desired distance, in accordance with aspects of the present disclosure.

This example describes fluid focus mechanisms for achieving a desired separation between sample-containing droplets as they pass through a fluorescence detection system; see FIGS. 12-14. As the discussion above indicates, it may be desirable for droplets within a detection region to be separated by some known average distance, or at least by some approximate minimum distance. For example, adequate spacing may permit split beams of radiation and/or detectors to be disposed most appropriately, and may allow a suitable choice of adjustment range for an adjustable mirror, when one is used.

In addition, proper spacing can help to avoid unintentionally detecting radiation from two or more droplets simultaneously, which can result in false positives and other errors in the detection system. For instance, as described previously, an uncleaved probe within a droplet still emits some amount of fluorescence even though the nucleic acid target is not present in the droplet. Thus, the intensity of fluorescence emitted from two or more droplets, neither of which contains a target, may be sufficient to trigger a positive detection result if the fluorescence from those multiple droplets is mistakenly thought to come from a single droplet. Other errors, such as errors in determining droplet volume and target concentration, also may result when droplets are spaced too closely together.

FIG. 12 shows a fluid focus mechanism, generally indicated at 480, which is configured to separate sample-containing droplets from each other by some desired amount of distance. This mechanism may be used, for example, to separate droplets prior to transferring them toward a detector intersection region such as intersection region 214 of FIG. 2, intersection region 264 of FIG. 4, or any of the other intersection regions described above. Focus mechanism 480 includes a droplet input channel 482, which contains sample-containing droplets 484 that are spaced closely together. Focusing fluid, indicated by arrows 486, is transferred through focus fluid input channels 488, 490, so that it encounters droplets from the droplet input channel at a focus region generally indicated at 492.

A droplet entering focus region 492 will be channeled into droplet egress channel 494, which is the only channel through which fluid can exit the focus region. Egress channel 494 may be configured to have regions with a smaller inner diameter 496 than the inner diameter of some or all of droplet input channel 482 and focus fluid input channels 488, 490, although in some instances this may not be the case. Because fluid is flowing into focus region 492 from focus fluid input channels 488 and 490 as well as from droplet input channel 482, and/or because egress channel 494 has a smaller cross sectional area than the other channels, fluid will flow more rapidly through the egress channel than through the other channels.

Because of the increase in fluid speed as fluid approaches the egress channel, droplets will accelerate as they enter the egress channel, and will become separated from each other as FIG. 12 indicates. By appropriate choices of channel inner diameters and focus fluid input velocity, essentially any desired average spacing between droplets can be achieved. Within egress channel 494, there may be an irradiation zone, generally indicated at 498. The irradiation zone may have features, such as increased transparency and/or thinner channel walls, which are conducive to irradiating droplets with radiation from a radiation source 500. A forward scatter detector 502 and a fluorescence detector 504 may be positioned appropriately to detect scattered and fluorescence radiation, as described previously.

FIG. 13 shows another fluid focus mechanism, generally indicated at 510. As in the case of fluid focus mechanism 480 of FIG. 12, fluid focus mechanism 510 is configured to increase the distance between closely spaced sample-containing droplets to some desired minimum average value. Fluid focus mechanism 510 includes a droplet input channel 512 that has a body portion 514 and a neck portion 516. Body portion 514 may be configured to contain a relatively large number of closely spaced sample-containing droplets 515, as FIG. 13 depicts, or in some cases it may contain a stream of continuously flowing droplets. In either case, the diameter of neck portion 516 may be chosen to substantially match, or to be just slightly larger than, the expected average droplet diameter, so that only one droplet at a time will typically be able to travel through the neck portion.

Mechanism 510 also includes an outer fluid channel 518, which surrounds at least a portion of droplet input channel 512, including neck portion 516. In conjunction with droplet input channel 512, outer fluid channel 518 defines a focus fluid input channel 520 between the droplet input channel and the outer fluid channel. Typically, droplet input channel 512 and outer fluid channel 518 will be cylindrical, so that focus fluid input channel 520 will take the form of a concentric cylindrical shell. Focusing fluid, generally indicated by arrows 522, may be transferred through focus fluid input channel 520 at a desired velocity. Accordingly, as each droplet 515 exits neck portion 516, it will accelerate away from the neck portion due to the flow of the focusing fluid. Through careful selection of the geometry of the system and the focusing fluid velocity, any desired separation between adjacent droplets exiting the neck portion can be attained. A radiation source 524, a forward scatter detector 526, and a fluorescence detector 528 may be provided to irradiate, track, and analyze droplets as described previously.

FIG. 14 is a section of fluidic tubing 540 illustrating how an appropriate choice of fluid channel diameter(s) can contribute to an appropriate separation between droplets. This point was discussed above, in the description of neck portion 516 of fluid focus mechanism 510. This description applies not only to a neck portion of a droplet input channel, but also more generally to any fluid channel through which droplets pass within a detection system according to the present disclosure. For example, the same considerations apply to fluid channel 512 of FIG. 2, fluid channel 262 of FIG. 4, etc.

As FIG. 14 depicts, fluidic tubing 540 may be selected to have an inner diameter that is correlated with the expected average droplet diameter. Accordingly, a droplet 542 having a slightly smaller than average diameter will be relatively unlikely to be in close proximity to additional droplets in the tubing. Similarly, a droplet 544 having the expected average diameter will move freely within tubing 540, and will maintain its spherical shape. Finally, a droplet 546 having a diameter slightly greater than the expected average diameter will take on a partially cylindrical shape, the volume of which may be estimated accordingly. Thus, an appropriate choice of fluid tubing size can help to ensure proper separation between droplets.

EXAMPLE 5

Batch Fluorescence Detection

In some cases, it may be desirable to irradiate and/or detect fluorescence from sample-containing droplets in relatively large batches rather than one droplet at a time. This example describes a system for detecting fluorescence emitted from a plurality of droplets that have been transferred to a chamber for batch detection; see FIG. 15.

FIG. 15 schematically depicts a batch optical detection system, generally indicated at 560. In contrast to the previously described continuous flow detection systems, in which sample-containing droplets flow continuously through an intersection region where excitation radiation intersects the path of the moving droplets, system 560 is configured to detect radiation from a plurality of droplets that have been collected in a detection region, and in some cases temporarily stopped from flowing through the system. This allows the fluorescence level of many droplets to be detected in a single detection operation, which may be advantageous in some applications.

Batch detection system 560 includes a droplet input channel 562, within which sample-containing droplets 564 may be caused to flow in an emulsion (such as a water-in-oil emulsion), just as in the previously described detection systems. System 560 also includes a valve mechanism, generally indicated at 566, which is configured to selectively direct droplets toward either of two fluorescence detection chambers 568, 570. For example, valve mechanism 566 may include a first valve 572 disposed between droplet input channel 562 and detection chamber 568, and a second valve 574 disposed between droplet input channel 562 and detection chamber 570. Thus, by opening and closing valves 572 and 574 appropriately, droplets may be transferred selectively into chambers 568, 570. This may allow a substantially continuous flow of emulsion to be transferred from the droplet input fluid channel to the fluorescence detection chambers.

Chambers 568, 570 may be configured to have a relatively shallow depth, to allow substantially only a monolayer of droplets within each chamber, so that only one droplet is disposed within each portion of the line of sight of a detector and is confined to the focal plane of the detector. Alternatively, various three-dimensional detection configurations, such as confocal imaging or wide-field imaging with deconvolution, may be used with non-monolayer samples.

A radiation source 576 is configured to illuminate droplets within chambers 568, 570, and after a desired number of droplets are transferred into one of the detection chambers, the chamber may be illuminated with radiation from source 576. Source 576 may be configured in various ways to illuminate substantially all of the droplets within a chamber. For example, radiation source 576 may include a single radiation emitting element, configured to illuminate substantially the entire chamber either by emitting a broad beam of radiation or by emitting radiation toward intermediate optics (not shown) that spread the emitted beam to cover the entire chamber. The radiation source also may include a plurality of radiation emitting elements, such as lasers, LEDs, and/or lamps, among others, each configured to illuminate a portion of the appropriate detection chamber. Alternatively or in addition, one or more radiation emitting elements of radiation source 576 may be configured to scan the chamber, to sequentially illuminate droplets within the chamber, or the chamber itself may be configured to move so that all portions of the chamber intersect a substantially stationary beam of radiation. In some cases, a combination of two or more of the above techniques may be effective.

A fluorescence detector 578 is provided and configured to detect fluorescence emitted from droplets 564. As has been described previously, the amount of fluorescence emitted by a particular droplet is expected to be significantly higher if the droplet contains a target nucleotide sequence, because in that case the corresponding fluorescent probe will typically have been cleaved from its associated quenching molecule. Thus, after the droplets within a detection chamber have been illuminated with stimulating radiation or in some cases while illumination is occurring, detector 578 may be configured to receive fluorescence from the detection chamber. As in the case of illumination, detection may proceed in various ways. For example, a large format detector such as a CCD focal plane array may be used to detect radiation emitted from an entire detection chamber simultaneously. Alternatively, a smaller detector such as a photodiode or a photomultiplier may be scanned across the chamber, or the chamber may be repositioned with respect to the detector, to detect fluorescence radiation from various portions of the detection chamber sequentially.

System 560 may be configured to allow substantially continuous flow through droplet input channel 562, by transferring droplets into two or more detection chambers, such as chambers 568, 570, sequentially. For example, FIG. 15 depicts the system at a time when chamber 568 has already been filled with droplets and is being illuminated and/or imaged, whereas chamber 570 is in the process of being filled. Accordingly, valve 572 will be in its closed position, and valve 574 will be in its open position, to allow droplets to flow into chamber 570.

Upon completion of the detection process on the droplets within chamber 568, valve 574 may be closed, valve 572 may be opened, and another valve 580 at the distal end of chamber 568 also may be opened. This stops the flow of droplets into chamber 570 and restarts the flow of droplets into chamber 568, while allowing the droplets already in chamber 568 to escape through distal valve 580. Another distal valve 582 may be disposed at the end of chamber 570 for a similar purpose. Alternatively, before the flow of droplets into a given chamber is resumed, and while droplets are still flowing into the other chamber, the chamber not receiving droplets may be washed with a fluid that enters through another fluid channel (not shown). This may help to avoid the possibility of mistakenly illuminating and detecting the same droplet twice. With or without a wash step, coordinated motions of valves as described above may allow an emulsion of sample-containing droplets to be continuously transferred in and out of any desired number of detection chambers.

Batch fluorescence detection may be performed without actually stopping droplets within the detection chambers of the system. For example, even if valves 580, 582 are not provided or are left open, droplets entering one of chambers 568, 570 may slow sufficiently to allow batch detection, and the lateral width of the detection chambers may be chosen to facilitate this. Alternatively or in addition, various particle tracking algorithms may be used to track droplets as they move within the detection chambers. Furthermore, a batch detection system may be partially or completely fluidically decoupled from other portions of a molecular amplification system. For example, a simple array of droplet-containing wells or reservoirs (such as a plate array) may be placed in a fluorescence detection region and imaged as described above.

EXAMPLE 6

Detection Methods

Figure 16:
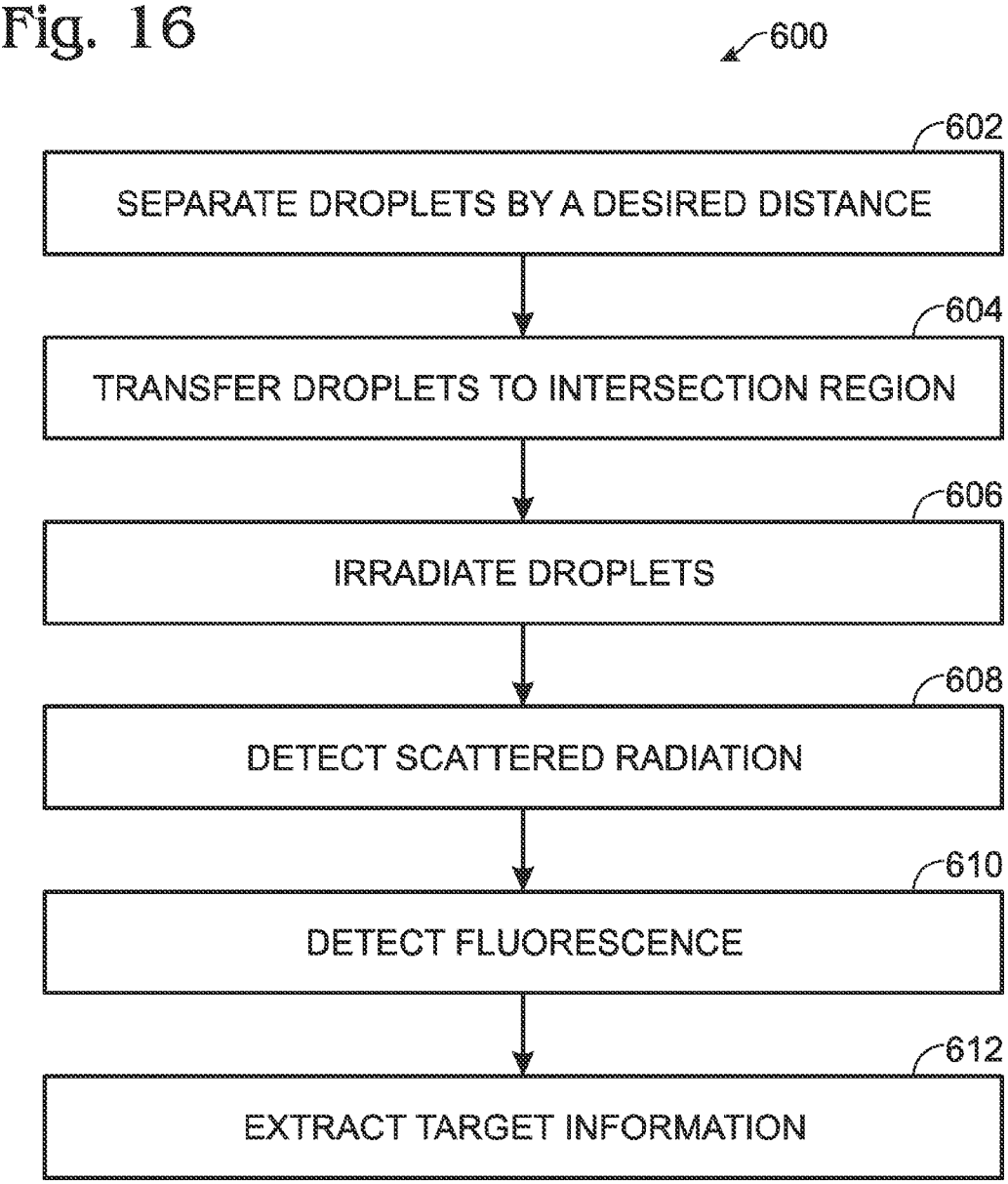
FIG. 16 is a flow chart depicting a method of detecting fluorescence from sample-containing droplets, in accordance with aspects of the present disclosure.

This example describes a method of detecting fluorescence from sample-containing droplets that have undergone PCR thermocycling; see FIG. 16.

FIG. 16 is a flowchart depicting the steps of a fluorescence detection method, generally indicated at 600, which may be performed in conjunction with a PCR system of DNA amplification according to the present disclosure. Although various steps of method 600 are described below and depicted in FIG. 16, the steps need not necessarily all be performed, and in some cases may be performed in a different order than the order shown in FIG. 16.

At step 602, sample-containing droplets are separated by a desired average distance. This may be accomplished, for example, by various flow focusing techniques such as those described above (i.e., by flow focusing the droplets as they are generated), and/or by generating droplets at a suitable rate. In cases of batch detection such as in a stop-flow system, it may be appropriate for droplets to remain closely spaced during fluorescence detection, and accordingly a droplet separation step may not be performed.

At step 604, the sample-containing droplets are transferred into a radiation intersection region, within which they will be exposed to illuminating radiation chosen to stimulate emission of fluorescence radiation from one or more fluorescent probes within the droplets, with an intensity that depends in part on whether or not a quenching moiety has been cleaved from the probe due to polymerase binding of the associated nucleotide target primer. In the case of continuous flow detection, the intersection region may be disposed within a fluid channel such as a capillary tube. In the case of batch detection, the intersection region may be disposed within one or more detection chambers. In this case, transferring droplets into the intersection region may include steps such as opening and closing one or more valves to allow a continuous flow of droplets into and out of the intersection region.

At step 606, the droplets in the radiation intersection region encounter and are irradiated with stimulating radiation, which includes at least one wavelength chosen to excite the fluorescent probe(s) known to be present in the reagents within the droplets. As described above, the illuminating radiation may be produced by a laser, and LED, or any other suitable radiation source, and may be transferred to the intersection region through free space or through one or more optical fibers. Furthermore, the radiation may be focused, diverged, split, filtered, and/or otherwise processed before reaching the intersection region, to efficiently irradiate the droplets in the most suitable manner for a particular detector system configuration.

At step 608, radiation scattered from the droplets in the intersection region may be detected by a forward scattering detector. This step will typically not be performed in a batch detection system, where each droplet is approximately stationary or at least relatively slow moving in a detection chamber that serves as the radiation intersection region. However, detecting scattered radiation in a continuous flow detection system may help to correlate simultaneous or subsequent fluorescence detection with the presence of droplets in the intersection region, and may allow the volume and target molecule concentration of each droplet to be estimated, as described above. More generally, step 608 may include performing any measurement to enable an estimation of the volume of each droplet, such as the amount of radiation scattered from the droplet, the time of flight of the droplet as it passes through the intersection region, an electrical property of the droplet, or a thermal property of the droplet. Method 600 also may include estimating the volume of each droplet based on the measurement performed in step 608.

At step 610, fluorescence emitted by droplets irradiated in the intersection region is detected by a fluorescence detector. As described in the preceding examples, the emitted radiation may be transferred to the fluorescence detector with or without passing through one or more intermediate optical elements such as lenses, apertures, filters, or the like. The emitted radiation also may or may not be transferred to the fluorescence detector through one or more optical fibers. In batch detection applications, the detector and/or the intersection region may be configured to move in a manner that allows an optical scan of the intersection region by a detector having a smaller field of view than the entire intersection region.

At step 612, detected fluorescence is analyzed to determine whether or not a particular target nucleotide sequence was present in the droplets. Additional information, including but not limited to an estimate of the number or fraction of droplets containing a target molecule, the average concentration of target molecules in the droplets, an error margin, and/or a statistical confidence level, also may be extracted from the collected data.

Using the data collected from each droplet in an analysis may be conditional and may depend, for example, on whether the estimated volume of the droplet falls within a particular predetermined range. More specifically, if the estimated volume of a droplet falls within a predetermined range, then the fluorescence intensity emitted by that droplet may be used in a determination of target molecule concentration in the sample, whereas if the estimated volume of the droplet falls outside the predetermined range, then the fluorescence intensity emitted by the droplet may be excluded from a determination of target molecule concentration in the sample.

EXAMPLE 7

Exemplary Transport System for Detection

Figure 17:
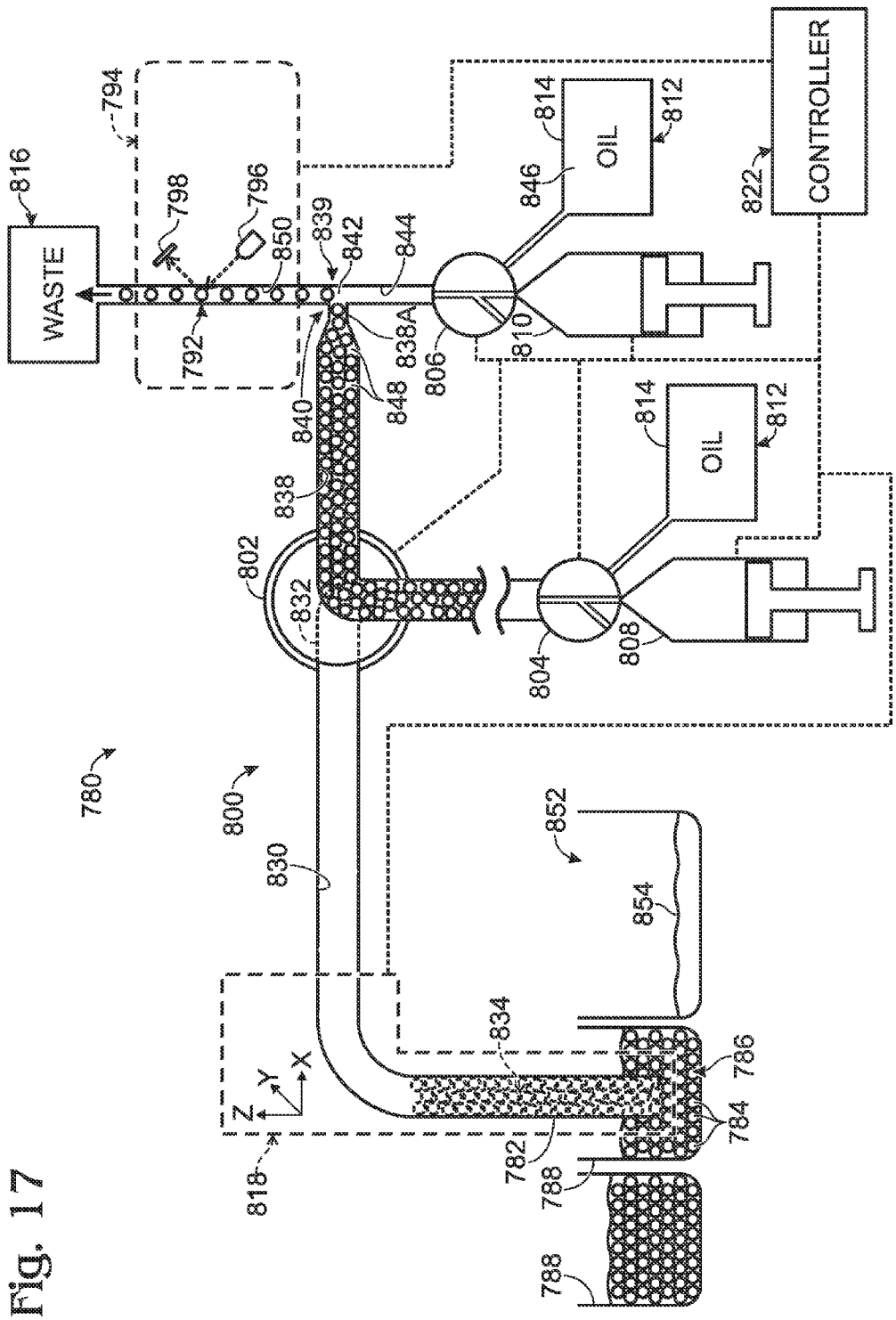
FIG. 17 is a schematic view of selected aspects of an exemplary droplet transport system for picking up droplets from a container, increasing the distance between droplets, and driving the droplets serially through an examination region for detection, in accordance with aspects the present disclosure.

This example describes an exemplary transport system 80 for loading droplets, spacing droplets, and driving the spaced droplets to an examination region for detection; see FIG. 17.

Transport system 780 is configured to utilize a tip 782 to pick up droplets 784 in an emulsion 786 held by at least one container 788. The droplets may be queued and separated in a droplet arrangement region 790, and then conveyed serially through an examination region 792 for detection of at least one aspect of the droplets with at least one detection unit 794. The detection unit may include at least one light source 796 to illuminate examination region 792 and/or fluid/droplets therein, and at least one detector 798 to detect light received from the illuminated examination region (and/or fluid/droplets therein).

The transport system may include a channel network 800 connected to tip 782. The channel network may include channel-forming members (e.g., tubing and/or one or more chips) and at least one valve (e.g., valves 802-806, which may include valve actuators) to regulate and direct fluid flow into, through, and out of the channel network. Fluid flow into, through, and out of channel network 800 may be driven by at least one pressure source (to apply negative pressure and/or positive pressure), generally, a pump, such as a sample pump 808 and a dilution pump 810. The fluid introduced into channel network 800 may be supplied by emulsion 786 and one or more fluid sources 812 formed by reservoirs 814 and operatively connected to one or more of the pumps. (A cleaning fluid also may be introduced via the tip.) Each fluid source may provide any suitable fluid, such as a hydrophobic fluid (e.g., oil), which may be miscible with the continuous phase of the emulsion and/or a carrier phase in the system, but not the dispersed phase of the droplets, or may provide a relatively more hydrophilic fluid for cleaning portions of the channel network and/or tip. Fluid that travels through examination region 792 may be collected in one or more waste receptacles 816.

The continuous phase, carrier fluid, and/or dilution fluid may be referred to as oil or an oil phase, which may include any liquid (or liquefiable) compound or mixture of liquid compounds that is immiscible with water. The oil may be synthetic or naturally occurring. The oil may or may not include carbon and/or silicon, and may or may not include hydrogen and/or fluorine. The oil may be lipophilic or lipophobic. In other words, the oil may be generally miscible or immiscible with organic solvents. Exemplary oils may include at least one silicone oil, mineral oil, fluorocarbon oil, vegetable oil, or a combination thereof, among others. In exemplary embodiments, the oil is a fluorinated oil, such as a fluorocarbon oil, which may be a perfluorinated organic solvent. A fluorinated oil includes fluorine, typically substituted for hydrogen. A fluorinated oil may be polyfluorinated, meaning that the oil includes many fluorines, such as more than five or ten fluorines, among others. A fluorinated oil also or alternatively may be perfluorinated, meaning that most or all hydrogens have been replaced with fluorine. An oil phase may include one or more surfactants.

Each pressure source or pump may have any suitable structure capable of driving fluid flow. The pump may, for example, be a positive-displacement pump, such as a syringe pump, among others. Other exemplary pumps include peristaltic pumps, rotary pumps, or the like.

The position of tip 782 may be determined by a drive assembly 818 capable of providing relative movement of the tip and container(s) 788 along one or more axes, such as three orthogonal axes 820 in the present illustration. In other words, the drive assembly may move the tip while the container remains stationary, move the container while the tip remains stationary, or move both the tip and the container at the same or different times, among others. In some embodiments, the drive assembly may be capable of moving the tip into alignment with each container (e.g., each well of a multi-well plate), lowering the tip into contact with fluid in the container, and raising the tip above the container to permit movement of the tip to another container. The drive assembly may include one or more motors to drive tip/container movement, and one or more position sensors to determine the current position of the tip and/or container and/or changes in tip/container position. Accordingly, the drive assembly may offer control of tip position in a feedback loop.

Transport system 780 further may include a controller 822. The controller may control operation of, receive inputs from, and/or otherwise communicate with any other components of the transport system, such as detection unit 794, valves 802-806 (e.g., via actuators thereof), pumps 808 and 810, and drive assembly 818, among others. For example, the controller may control light source operation and monitor the intensity of light generated, adjust detector sensitivity (e.g., by adjusting the gain), process signals received from the detector (e.g., to identify droplets and estimate target concentrations), and so on. The controller also or alternatively may control valve positions, tip movement (and thus tip position), pump operation (e.g., pump selection, direction of flow (i.e., generation of positive or negative pressure), rate of flow, volume dispensed, etc.), and the like. The controller may control when, where, and how fluid moves within the channel network 800. The controller may provide automation of any suitable operation or combination of operations. Accordingly, the transport system may be configured to load and examine a plurality of emulsions automatically without user assistance or intervention.

The controller may include any suitable combination of electronic components to achieve coordinated operation and control of system functions. The electronic components may be disposed in one site or may be distributed to different areas of the system. The controller may include one or more processors (e.g., digital processors, also termed central/computer processing units (CPUs)) for data processing and also may include additional electronic components to support and/or supplement the processors, such as switches, amplifiers, filters, analog to digital converters, busses, one or more data storage devices, etc. In some cases, the controller may include at least one master control unit in communication with a plurality of subordinate control units. In some cases, the controller may include a desktop or laptop computer. In some cases, the controller only may process data. The controller may be connected to any suitable user interface, such as a display, a keyboard, a touchscreen, a mouse, etc.

Channel network 800 may include a plurality of channels or regions that receive droplets as the droplets travel from tip 782 to waste receptacle 816. The term "channel" may be used interchangeably with the term "line" in the explanation and examples to follow.

Tip 782 may form part of an intake channel or loading channel 830 that extends into channel network 800 from tip 782. Droplets may enter other regions of the channel network from loading channel 830. Droplets 784 in emulsion 786 may be introduced into loading channel 830 via tip 782 (i.e., picked up by the tip) by any suitable active or passive mechanism. For example, emulsion 786 may be pulled into the loading channel by a negative pressure created by a pump, i.e., by suction (also termed aspiration), may be pushed into the loading channel by a positive pressure applied to emulsion 786 in container 788, may be drawn into the loading channel by capillary action, or any combination thereof, among others.

In exemplary embodiments, pump 808 pulls the emulsion into loading channel 830 by application of a negative pressure. To achieve loading, valve 802 may be placed in a loading position indicated in phantom at 832, to provide fluid communication between tip 782 and pump 808. The pump then may draw the emulsion, indicated by phantom droplets at 834, into loading channel 830 via tip 782, with the tip in contact with the emulsion. The pump may draw the loaded droplets through valve 802 into a holding channel 836.

The loaded droplets may be moved toward detection unit 794 by driving the droplets from holding channel 836, through valve 802, and into a queuing channel 838 that extends to an inlet channel 838A of a spacer 839, which in this case is T-shaped. Inlet channel 838A may place the droplets in single file, indicated at 840.

The droplets may enter a confluence region or separation region 842 of spacer 839, optionally in single file, as they emerge from inlet channel 838A. The confluence region may be formed at a junction of the inlet channel and at least one dilution channel 844. The dilution channel may supply a stream of dilution fluid 846 driven through confluence region 842, as droplets and carrier fluid/continuous phase 848 enter the confluence region as a stream from inlet channel 838A. The dilution fluid may be miscible with the carrier fluid and serves to locally dilute the emulsion in which the droplets are disposed, thereby increasing the average distance between droplets.

The spacer may define a minimum diameter of a flow path that droplets follow from tip 782 through examination region 792, and optionally to a waste receptacle downstream of the examination region. Further aspects of spacers are described below in Examples 8-11. The droplets may enter an examination channel 850 after they leave spacer 839.

The examination channel may include examination region 792, where the examination channel may be illuminated and light from the examination region may be detected.

Tip 782 may be utilized to load a series of emulsions from different containers. After droplets are loaded from a first container, the tip may be lifted to break contact with remaining fluid, if any, in the container. A volume of air may be drawn into the tip to serve as a barrier between sets of loaded droplets and/or to prevent straggler droplets from lagging behind as the droplets travel through the channel network. In any event, the tip next may be moved to a wash station 852, wherein tip 782 may be cleaned by flushing, rinsing, and/or immersion. More particularly, fluid may be dispensed from and/or drawn into the tip at the wash station, and the tip may or may not be placed into contact with a fluid 854 in the wash station during cleaning (e.g., decontamination). The cleaned tip then may be aligned with and lowered into another container, to enable loading of another emulsion.

A transport system may include any combination of at least one vessel (i.e., a container) to hold at least one emulsion (and/or a set of vessels to hold an array of emulsions), at least one pick-up tip to contact the emulsion(s) and receive droplets from the emulsion, one or more fluid drive mechanisms to generate positive and/or negative (i.e., one or more pumps to pull and/or push fluid into or out of the tip and/or through a detection site), a positioning mechanism for the tip and/or vessel (to move the tip with respect to the vessel or vice versa), one or more valves to select and change flow paths, at least examination region to receive droplets for detection, or any combination thereof, among others.

EXAMPLE 8

Detection System with a Cross-Shaped Spacer

This example describes an exemplary detection system including a cross-shaped spacer; see FIGS. 18 and 19. The detection system in this example and in Examples 9-11 also or alternatively may be described as a transport system for detection and may include any combination of the components, features, and capabilities of the transport systems described in Example 7 and in U.S. Provisional Patent Application Ser. No. 61/467,347, filed Mar. 24, 2011, which is incorporated herein by reference.

FIG. 18 shows an exemplary detection system 870 including a cross-shaped spacer 872 positioned upstream of an examination region or irradiation zone 874. Droplets 876 may be placed in single file and separated from each other by spacer 872. The separated droplets then may travel serially through examination region 874 where they are illuminated with at least one light source 876. Light from the droplets and/or examination region may be detected by at least one detector 878.

Spacer 870 may include a droplet inlet channel 880, a pair of dilution channels 882, and a droplet outlet channel 884. A confluence region 886 may be formed where the channels meet.

In operation, an emulsion 888 containing droplets 876 flows along droplet inlet channel 880 to confluence region 886. Inlet channel 880 may include neck region, such as a tapered region 888 and a uniform region 890, in which the droplets may be disposed in single file before they enter confluence region 886. The uniform region may be of substantially uniform diameter and may define a minimum diameter of a flow path followed by droplets from a tip to an examination region of a detection system (e.g., see FIG. 17).

Dilution channels 882 supply a dilution fluid 892, such as oil, to the confluence region. The dilution fluid dilutes emulsion 888 locally, which increases the average distance between the droplets and may accelerate each droplet out of the confluence region into droplet outlet channel 884. The spacer reduces the density of the droplet emulsion (i.e., reduces the number of droplets per μL and/or per unit length of the flow path). This dilution may be advantageous when droplet detection occurs in a flow-through detector as it reduces the rate at which coincident droplets pass through the examination region.

Examination region 874 may be formed by an examination channel 894 that extends from droplet outlet channel 884. The examination channel may be discrete from the droplet outlet channel and may have the same or a different diameter, such as a larger diameter as shown here.

Droplet inlet channel 880 may have any suitable shape and size. Tapered region 888 of channel 880 may converge in a substantial cone from a diameter of two or more droplet diameters to a minimum diameter of approximately one droplet diameter or less than one droplet diameter. Uniform region 890 may define a minimum diameter of the flow path followed by droplets, and may extend for any suitable length such as at least one droplet (or channel) diameter, two or more droplet (or channel) diameters, or at least about three droplet (or channel) diameters, among others. Exemplary lengths may include between about one-half and three average droplet diameters, between about one and two droplet average diameters, and between about five-fourths and two average droplet diameters, among others. A relatively longer uniform region of the droplet inlet channel may permit greater droplet stabilization before droplets are subjected to shear force in the confluence region.

Dilution channels 882 may have any suitable diameter. Channels 882 may, for example, be about one-fifth of the droplet diameter to about two droplet diameters, among others. In some examples, the droplets may be about 125 microns in diameter and the oil channels about 25 microns to about 250 microns in diameter. Shear produced in the confluence region by inflow of dilution fluid can be reduced by increasing the diameter of the dilution channels, but if the diameter is too large, two droplets can pass through together. Generally, smaller diameter channels and/or higher flow rates can cause higher shear stresses.

Droplet outlet channel 884 may have any suitable size(s). Channel 884 may have a diameter that is about the same as or greater than the minimum diameter of droplet inlet channel 880.

Examination channel 894 also may have any suitable size. Channel 894 may have a diameter that is about the same as or larger than the diameter of droplet outlet channel 884. A greater diameter of the examination channel may cause the droplets to slow down before they reach examination region 874, which may permit more accurate measurements. Accordingly, examination channel 894 may have a diameter that is about the same as the diameter of droplets 876, to keep droplets centered in the channel as they pass through the examination region. In any event, the diameter of the examination region may be about one-half to two droplet diameters, among others. Generally, an examination region with a smaller diameter can improve detection uniformity because the positional variation of droplets laterally within the examination region is reduced. Also, an examination region with a smaller diameter (e.g., the diameter of the droplet or smaller) can reduce the ability of intact droplets to catch up with coalesced droplets, which may travel more slowly. Droplet outlet channel 884 and examination channel 894 may be formed by discrete structures, such as a connector and tubing, respectively (see below).

The distance between confluence region 886 and examination region 874 may be a compromise between droplet stabilization and droplet separation. If the examination region is too close to the confluence region, droplet shape may not have stabilized yet. On the other hand, if the examination region is too far from the confluence region, droplets may travel at different rates, which may cause droplets to cluster. In exemplary embodiments, the examination region is at least about five droplet diameters from the separation region and less than about 1000 droplet diameters away. Generally, the optimal distance between the confluence region and the examination region depends on the size of the droplet and the amount of shear stress generated by the dilution fluid in the confluence region.

Any suitable flow rates of the emulsion and dilution fluid may be used. The emulsion flow rate in the droplet inlet channel may depend on the viscoelastic stability of the droplets. Increased surface tension (liquid-liquid) or increased moduli (membrane) allow for higher shear on the droplets without rupture. Accordingly, droplets that have a higher viscoelastic stability, such as droplets encapsulated by a skin, may be substantially more stable to higher flow rates than those with a lower viscoelastic stability and/or without a skin. Further aspects of droplets encapsulated by a skin are described in U.S. patent application Ser. No. 12/976,827, filed Dec. 22, 2010, which is incorporated herein by reference. A suitable flow rate for the dilution fluid in dilution channels 882 depends on the diameter of the dilution channels, droplet size, diameter of the examination region, etc. Exemplary flow rates for the dilution fluid are about one-half to ten times the flow rate of the emulsion into the confluence region. Relatively higher flow rates may be advantageous in the removal of debris that can clog droplet inlet channel 880, tapered region 888 and/or uniform region 890 thereof. On the other hand, relatively higher flow rates can produce shear stresses that can reduce droplet integrity by causing droplets to either break up or coalesce. Low flow rates can reduce shear stress and in turn preserve droplet integrity but produce less droplet separation.

Droplet inlet channel 880 and dilution channels 882 may extend to confluence region 886 at any suitable angles. For example, the dilution channels may be substantially perpendicular to the droplet inlet channel or each may form an angle of about 30 to 90 degrees with the droplet inlet channel.

FIG. 19 shows a somewhat schematic embodiment of a cross-shaped spacer 910 that may be included in detection system 870 of FIG. 18. Spacer 910 may be formed by a discrete connector 912 that provides fluid communication between droplet inlet tubing 914, dilution inlet tubing 916, and droplet outlet tubing 918. Any of the tubing may be described as a tube and/or a capillary. Connector 912 may define at least a portion of droplet inlet channel 880 (particularly tapered region 888 uniform region 890), dilution inlet channels 882, droplet outlet channel 884, and separation region 886. Accordingly, inlet tubing 914 supplies droplets, dilution tubing 916 supplies a dilution fluid, and droplet outlet tubing 918 receives separated droplets and may carry the separated droplets to an examination region formed by the outlet tubing.

The connector also may define a counterbore 919 for each channel, with the counterbore sized to receive an end of a piece of tubing (i.e., tubing 914, 916, or 918) and a fitting 920. The counterbore may include an internal thread 922 that engages an external thread of the fitting to secure the tubing to the connector with a fluid-tight seal.

Connector 912 may be formed of any suitable material. In some embodiments, the connector may be formed of a polymer (plastic). The polymer may be hydrophobic or a hydrophobic coating may be added to surfaces of the channels. The connector may be formed by machining a block of material and a smooth finish may be formed on machined inner surfaces.

Outlet tubing 918 may form examination region 874 (see FIG. 18). Outlet tubing 918 of larger diameter may offer the advantage of lower resistance to flow, enabling the system to run at lower pressures, which can simplify the design and lower the cost of the system. In contrast, connector 912 may provide a "choke point," namely, a minimum diameter, where the diameter is less than the diameter of the outlet tubing (and/or inlet tubing). The use of a choke point can be advantageous because it simplifies the location of clogs and their removal. Also, placing the choke point in a discrete component, such as connector 912, permits removal of clogs by replacing and/or servicing only the component. On the other hand, outlet tubing of smaller diameter requires a lower singulation ratio (the ratio of the flow rates of the dilution fluid to the emulsion) because less dilution fluid and/or continuous phase is required between the droplets and the tubing wall.

EXAMPLE 9

Detection System with a T-shaped Spacer

Figure 20:
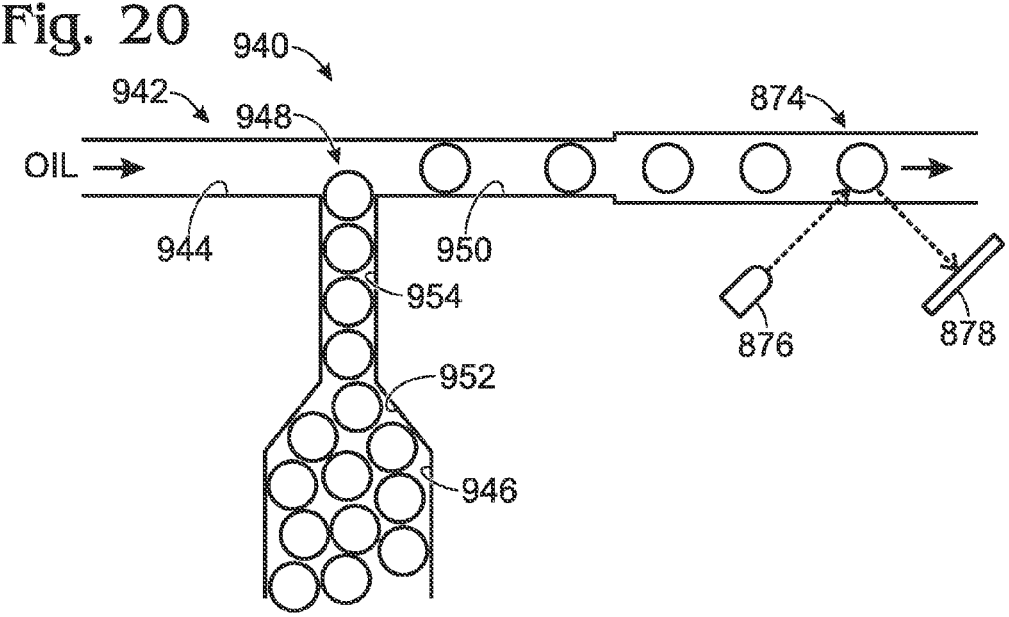
FIG. 20 is a schematic view of an exemplary detection system including a T-shaped spacer positioned upstream of an examination region, in accordance with aspects of the present disclosure.
Figure 21:
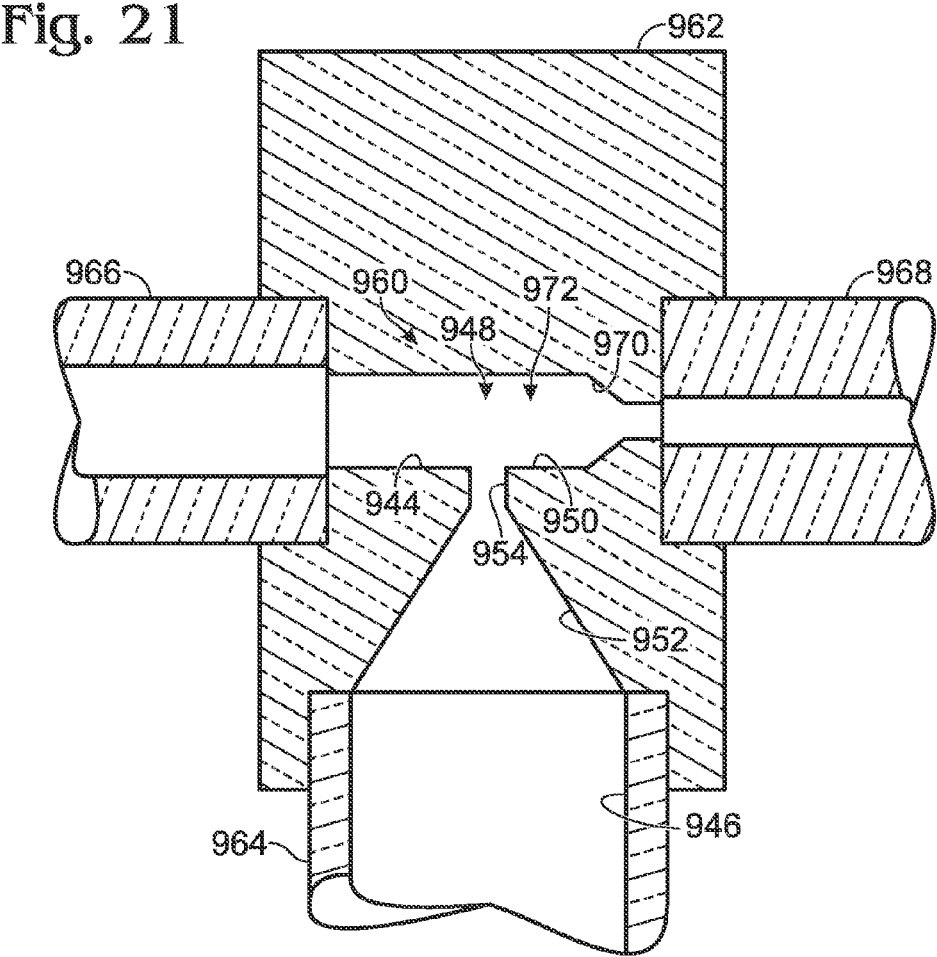
FIG. 21 is a sectional view of another exemplary T-shaped spacer that may be included in the detection system of FIG. 20, in accordance with aspects of the present disclosure.

This example describes an exemplary detection system including a T-shaped spacer; see FIGS. 20 and 21.

FIG. 20 shows an exemplary detection system 940 including a spacer 942 disposed upstream of examination region 874. The examination region is operatively connected to a light source 876 and a detector 874 as described above for detection system 870 of FIG. 18.

Spacer 942 may be structured and operates generally as described above for spacer 872 but differs in having only one dilution inlet channel 944, instead of two. Dilution channel 944 and a droplet inlet channel 946 meet at a confluence region 948 that joins a droplet outlet channel 950. Droplet inlet channel 946 may include a tapered region 952 and a uniform region 954, which may place droplets in single file. The dilution fluid may dilute the emulsion in the confluence region. Dilution channel 944 and droplet outlet channel 950 may or may not be coaxial. Also, droplet inlet channel 946 may join the dilution inlet channel and droplet outlet channel at any suitable angle including 90 degrees as shown here, or obliquely. Accordingly, spacer 942 may be described at being T-shaped, although the "T" may be distorted to be more Y-shaped in some embodiments.

FIG. 21 shows a somewhat schematic embodiment of a T-shaped spacer 960 that may be included in detection system 940 of FIG. 20. Spacer 960, like spacer 910 above (see FIG. 19), may be formed by a discrete connector 962. Connector 962 may have any of the properties or features described above for connector 912. (Fittings 920 have been omitted to simplify the presentation (see FIG. 19).) Connector 962 may provide fluid communication between droplet inlet tubing 964, dilution inlet tubing 966, and droplet outlet tubing 968. The connector may define at least a portion of dilution inlet channel 944, droplet inlet channel 946, confluence region 948, and droplet outlet channel 950. Here, droplet outlet channel 950 includes a tapered region 970 that tapers away from confluence region 948.

A region 972 of droplet outlet channel adjacent confluence region 948 may have a diameter that is at least 25% larger in diameter than the desired droplet size. This feature may cause any bolus of aqueous fluid entering the confluence region only to generate droplets that are significantly larger than the target droplet size. The T-shaped separator configuration may maintain significant force for separating droplets at up to two times the target droplet diameter. The exit constriction may be kept close to the introduction constriction so that any droplet that enters the droplet confluence region and region 972 will accelerate down the droplet outlet channel before the next droplet can enter the confluence region, effectively separating the droplets.

EXAMPLE 10

Detection System with Serial Spacers

Figure 22:
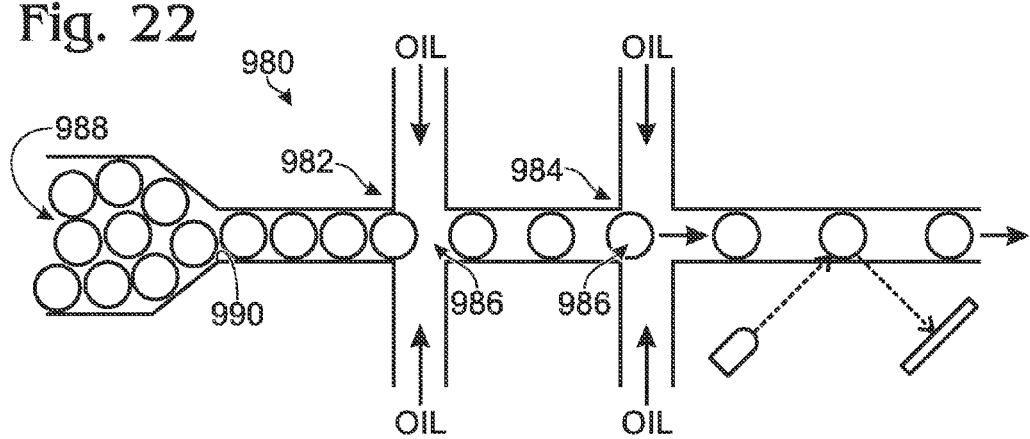
FIG. 22 is a schematic view of an exemplary detection system including multiple spacers arranged in series, in accordance with aspects of the present disclosure.
Figure 23:
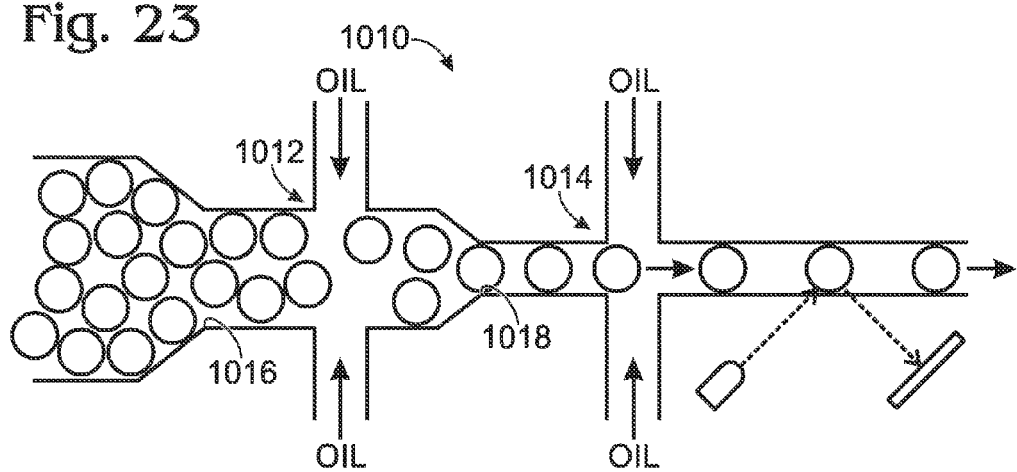
FIG. 23 is a schematic view of another exemplary detection system including multiple spacers arranged in series, in accordance with aspects of the present disclosure.
Figure 24:
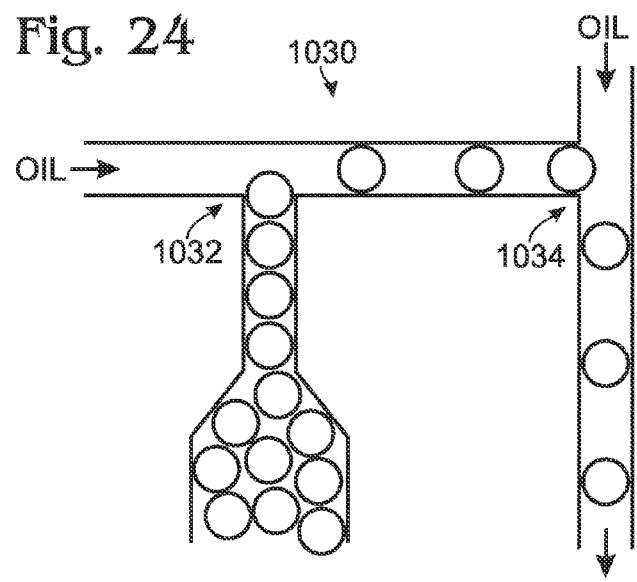
FIG. 24 is a schematic view of yet another exemplary detection system including multiple spacers arranged in series, in accordance with aspects of the present disclosure.

This example describes exemplary detection systems including serial spacers that increase the separation between droplets in two or more steps; see FIGS. 22-24.

FIG. 22 shows an exemplary detection system 980 including serial spacers 982, 984. Detection system 980 reduces the shear force exerted on droplets at each confluence region 986 by arranging two or more spacers in series. Each spacer dilutes emulsion 988; the average distance between droplets increases in multiple steps. Here, spacer 982 includes a neck region 990 that arranges droplets in single file before the droplets are separated. Spacer 984 further increases the average distance between droplets.

FIG. 23 shows another exemplary detection system 1010 including multiple spacers 1012, 1014. Here, both spacers include respective neck regions 1016, 1018. With this arrangement, droplets may be transitioned from multiple file to single file in two or more steps.

FIG. 24 shows yet another exemplary detection system 1030 including multiple spacers 1032, 1034 arranged in series. Each spacer has only one dilution inlet channel and is T-shaped. In other embodiments, spacers with different numbers of dilution inlet channels may be combined. For example, a T-shaped spacer may be combined with a cross-shaped spacer.

EXAMPLE 11

Selected Embodiments

This example describes additional aspects and features of systems for the detection of spaced droplets, presented without limitation as a series of numbered paragraphs. Each of these paragraphs can be combined with one or more other paragraphs, and/or with disclosure from elsewhere in this application, in any suitable manner. Some of the paragraphs below expressly refer to and further limit other paragraphs, providing without limitation examples of some of the suitable combinations.

1. A detection system for droplet-based assays, comprising: (A) a spacer including a droplet inlet channel, a droplet outlet channel, at least one dilution channel configured to supply a dilution fluid, and a confluence region formed at a junction of the droplet inlet channel, the droplet outlet channel, and the dilution channel, the spacer being configured such that an average distance of separation between droplets in the droplet outlet channel is greater than such average distance between droplets in the inlet channel; (B) a radiation source configured to irradiate droplets in an irradiation zone that is downstream of the droplet outlet channel; and (C) a detector configured to detect radiation from droplets disposed in the irradiation zone.

2. A detection system for droplets-based assays, comprising: (A) a droplet inlet channel; (B) a droplet outlet channel; (C) at least one dilution channel configured to supply a dilution fluid; (D) a confluence region formed at a junction of the droplet inlet channel, the droplet outlet channel, and the dilution channel, wherein the channels and the confluence region are configured such that an average distance of separation between droplets in the droplet outlet channel is greater than such average distance between droplets in the droplet inlet channel; (E) a radiation source configured to irradiate droplets in an irradiation zone that is downstream of the droplet outlet channel; and (F) a detector configured to detect radiation received from droplets disposed in the irradiation zone.

3. The system of paragraph 2, wherein the irradiation zone is of increased transparency to radiation from the radiation source relative the droplet outlet channel.

4. The system of paragraph 3, wherein the irradiation zone is formed by a channel having thinner walls in the irradiation zone relative to other regions of such channel.

5. The system of paragraph 2, wherein the droplet inlet channel has a minimum diameter near the confluence region, and wherein the droplet outlet channel has a diameter that is greater than the minimum diameter.

6. The system of paragraph 2, wherein the droplet inlet channel tapers toward the confluence region to form a neck region where droplets are disposed in single file.

7. The system of paragraph 6, wherein at least a portion of the neck region is conical.

8. The system of paragraph 2, wherein the irradiation zone is formed by a tube.

9. The system of paragraph 2, wherein the droplet inlet channel, the dilution channel, the droplet outlet channel, and the confluence region are defined by a same connector, and wherein tubing is connected to each of such channels and forms the irradiation zone.

10. The system of paragraph 9, wherein an end of the tubing is received in a respective counterbore defined by the connector for each of the channels.

11. The system of paragraph 2, wherein the at least one dilution channel includes a pair of dilution channels each extending to the confluence region.

12. A method of detection for droplets, comprising: (A) driving flow of an emulsion of droplets into a confluence region; (B) diluting the emulsion with a dilution fluid in the confluence region to increase an average distance between droplets; (C) irradiating the droplets in an irradiation zone disposed downstream of the confluence region; and (D) detecting radiation from the irradiation zone.

13. The method of paragraph 12, wherein the step of driving flow of an emulsion of droplets includes a step of disposing droplets in single file before such droplets reach the confluence region.

14. The method of paragraph 13, wherein the step of disposing droplets in single file includes a step of driving flow of droplets through an inlet channel including a neck region that tapers toward the confluence region.

15. The method of paragraph 12, further comprising a step of selecting an average distance of separation for the droplets in the irradiation zone and a step of establishing relative flow rates of the emulsion and the dilution fluid that achieve the average distance of separation with the steps of driving and diluting.

16. The method of paragraph 12, wherein the step of diluting includes a step of driving the dilution fluid into the confluence region from a pair of dilution channels.

17. The method of paragraph 12, wherein the irradiation zone is formed by tubing, wherein the step of irradiating is performed with a radiation source, and wherein the irradiation zone has increased transparency to radiation from the radiation source relative to other regions of the tubing.

18. The method of paragraph 12, wherein the step of detecting radiation includes a step of detecting light emitted from droplets.

19. The method of paragraph 12, wherein the droplets enter a droplet outlet channel as such droplets leave the confluence region, and wherein the droplet outlet channel has a diameter that is about the same as a diameter of the droplets.

20. The method of paragraph 12, wherein the step of driving flow includes a step of moving droplets from tubing to a discrete connector that forms the confluence region, wherein the step of diluting includes a step of driving flow of dilution fluid from tubing to the connector such that droplets travel from a droplet outlet channel formed by the connector to the irradiation zone formed by tubing.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of detection for droplet-based assays, the method comprising:
   placing an open end of a channel network into an emulsion;
   driving droplets of the emulsion along a flow path from the open end, through a confluence region where a dilution fluid is introduced into the flow path from at least one dilution inlet channel to increase an average distance between droplets, and through an examination region disposed downstream of the confluence region; and
   detecting light from the examination region as droplets pass through;
   wherein the channel network includes a droplet inlet channel that meets the at least one dilution inlet channel at the confluence region, and wherein the droplet inlet channel forms a tapered region that is sized such that droplets leave the tapered region in single file.

2. The method of claim 1, wherein the emulsion is held by a container, and wherein the step of placing an open end of a channel network is performed by moving the open end, the container, or both the open end and the container.

3. The method of claim 1, wherein the step of driving droplets includes a step of aspirating droplets of the emulsion into the channel network via the open end.

4. The method of claim 1, wherein the step of driving droplets includes a step of operating one or more syringe pumps.

5. The method of claim 1, wherein the step of detecting light is performed as droplets that are in single file pass serially through the examination region.

6. The method of claim 1, wherein the flow path has a minimum diameter between the tapered region and the confluence region.

7. The method of claim 6, further comprising a droplet outlet channel that extends from the confluence region, and wherein the droplet outlet channel has about a same diameter as the minimum diameter of the flow path.

8. The method of claim 6, wherein the minimum diameter is less than or approximately equal to the average diameter of the droplets.

9. The method of claim 8, wherein the minimum diameter is between about 90% and 100% of the average diameter of the droplets.

10. The method of claim 6, wherein the flow path is defined as least in part by at least two pieces of tubing and a discrete connector that provides fluid communication between at least a pair of ends of the at least two pieces of tubing, and wherein the minimum diameter is defined by the connector.

11. The method of claim 1, wherein the confluence region is formed at a junction where the droplet inlet channel, a droplet outlet channel, and the at least one dilution inlet channel meet one another.

12. The method of claim 1, wherein a portion of the flow path extends upward from the open end.

13. The method of claim 1, wherein the flow path has a smaller diameter in a region of the droplet inlet channel than in the examination region.

14. The method of claim 1, wherein the at least one dilution inlet channel includes a pair of dilution inlet channels.

15. A method of detection for droplet-based assays, the method comprising:
   placing an open end of a conduit into an emulsion;
   driving droplets of the emulsion along a flow path from the open end to an examination region; and
   detecting light from the examination region as droplets pass through;
   wherein the flow path is defined in part by a droplet inlet channel that forms a tapered region, and wherein the tapered region is sized such that droplets leave the tapered region in single file.

16. The method of claim 15, wherein the flow path has a smaller diameter in a region of the droplet inlet channel than in the examination region.

17. The method of claim 15, wherein a region of the droplet inlet channel downstream from the tapered region has a minimum diameter that is approximately equal to an average diameter of the droplets.

18. The method of claim 15, further comprising a step of introducing a dilution fluid into the flow path downstream of the tapered region to increase an average distance between droplets.

19. The method of claim 15, wherein the emulsion is held by a container, and wherein the step of placing an open end is performed by moving the open end, the container, or both the open end and the container.

20. A method of detection for droplet-based assays, the method comprising:
   placing an open end of a conduit into an emulsion;
   driving droplets of the emulsion into the conduit and along a flow path extending continuously from the open end to an examination region;
   introducing a dilution fluid into the flow path at a position upstream of the examination region to increase an average distance between droplets; and
   detecting light from the examination region as droplets pass through.

* * * * *